US012721684B2

(12) United States Patent
Ziv-Ari et al.

(10) Patent No.: US 12,721,684 B2
(45) Date of Patent: Sep. 1, 2026

(54) MULTIPLANE SUGGESTED ORIENTATION

(71) Applicant: Biosense Webster (Israel) Ltd., Yokneam (IL)

(72) Inventors: Morris Ziv-Ari, Atlit (IL); Nadav Barnea, Haifa (IL); Lior Zar, Poria Illit (IL); Hanna Cohen-Sacomsky, Zichron Ya'acov (IL); Shaked Meitav, Atlit (IL)

(73) Assignee: Biosense Webster (Israel) Ltd., Yokneam (IL)

(*) Notice: Subject to any disclaimer, the term of this patent is extended or adjusted under 35 U.S.C. 154(b) by 83 days.

(21) Appl. No.: 18/536,078

(22) Filed: Dec. 11, 2023

(65) Prior Publication Data

US 2025/0186126 A1 Jun. 12, 2025

(51) Int. Cl.

| | |
|---|---|
| ***A61B 34/20*** | (2016.01) |
| ***A61B 5/367*** | (2021.01) |
| ***A61B 8/08*** | (2006.01) |
| ***A61B 8/12*** | (2006.01) |

(52) U.S. Cl.

CPC .............. *A61B 34/20* (2016.02); *A61B 5/367* (2021.01); *A61B 8/0841* (2013.01); *A61B 8/085* (2013.01); *A61B 8/12* (2013.01); *A61B 2034/2063* (2016.02)

(58) Field of Classification Search

CPC ....... A61B 34/20; A61B 5/367; A61B 8/0841; A61B 8/085; A61B 8/12; A61B 2034/2063; A61B 8/4263; A61B 18/1492; A61B 34/25; A61B 8/0883

See application file for complete search history.

(56) References Cited

U.S. PATENT DOCUMENTS

| | | |
|---|---|---|
| 5,391,199 A | 2/1995 | Ben-Haim |
| 5,443,489 A | 8/1995 | Ben-Haim |
| 5,558,091 A | 9/1996 | Acker et al. |
| 6,172,499 B1 | 1/2001 | Ashe |
| 6,239,724 B1 | 5/2001 | Doron et al. |
| 6,332,089 B1 | 12/2001 | Acker et al. |
| 6,484,118 B1 | 11/2002 | Govari |
| 6,618,612 B1 | 9/2003 | Acker et al. |

(Continued)

OTHER PUBLICATIONS

Extended European Search Report issued on Apr. 14, 2025 for European Patent Application No. 24218540.3.

*Primary Examiner* — Amal Aly Farag
*Assistant Examiner* — Amal Farag
(74) *Attorney, Agent, or Firm* — Clayton, McKay & Bailey, PC

(57) ABSTRACT

Systems and methods for providing a multiplane suggested orientation by tracking a target are described. These include a catheter for performing medical electrophysiology, and a graphical user interface (GUI) for monitoring the catheter. The GUI is used to maintain the target in a display during medical electrophysiology. The catheter and GUI operate in combination to display a tilt angle to follow the target in the display, receiving a rotation angle of a current plane of a view of the device, receiving a point of interest related to the target, calculating a new plane using a vector in an axis after rotation and a vector from a center point of the device to the target, and calculating the angles between the rotation angle and an angle of the new plane to maintain inclusion of the target in the display.

20 Claims, 14 Drawing Sheets

(56) References Cited

U.S. PATENT DOCUMENTS

| | | | | |
|---|---|---|---|---|
| 6,690,963 | B2 | 2/2004 | Ben-Haim et al. | |
| 6,788,967 | B2 | 9/2004 | Ben-Haim et al. | |
| 6,892,091 | B1 | 5/2005 | Ben-Haim et al. | |
| 7,536,218 | B2 | 5/2009 | Govari et al. | |
| 7,540,288 | B2 | 6/2009 | Viswanathan et al. | |
| 7,756,576 | B2 | 7/2010 | Levin | |
| 7,848,787 | B2 | 12/2010 | Osadchy | |
| 7,869,865 | B2 | 1/2011 | Govari et al. | |
| 8,456,182 | B2 | 6/2013 | Bar-tal et al. | |
| 8,862,451 | B2 | 10/2014 | Alme et al. | |
| 9,186,081 | B2 | 11/2015 | Afonso et al. | |
| 9,980,652 | B2 | 5/2018 | Govari et al. | |
| 2008/0146941 | A1* | 6/2008 | Dala-Krishna ...... | A61B 8/4254 600/466 |
| 2008/0285824 | A1* | 11/2008 | Wildes ................. | A61B 8/4245 382/128 |
| 2015/0157408 | A1 | 6/2015 | Viswanathan et al. | |
| 2015/0173697 | A1* | 6/2015 | Parks ....................... | A61B 6/12 600/301 |
| 2020/0054399 | A1 | 2/2020 | Duindam et al. | |
| 2021/0187243 | A1 | 6/2021 | Park et al. | |
| 2023/0263580 | A1 | 8/2023 | Wendling et al. | |

* cited by examiner 458
450

454
456
452

MULTIPLANE SUGGESTED ORIENTATION

FIELD OF INVENTION

The present invention is related to medical systems and the imaging capabilities of and using devices during procedures. More particularly, the present invention relates to intra-body medical probes and ultrasound imaging providing a multiplane (e.g., at least two dimensions) suggested orientation.

BACKGROUND

Three-dimensional (3D) ultrasound is a medical ultrasound technique often used in, for example, fetal, cardiac, trans-rectal and intra-vascular applications. 3D ultrasound refers specifically to the volume rendering of ultrasound data. When involving a series of 3D volumes collected over time, it is commonly referred to as 4D ultrasound (three spatial dimensions plus one temporal dimension).

Ultrasound imaging may be used to image bodily tissue while a medical probe, inserted in the tissue, is used for performing a diagnostic or therapeutic procedure on the tissue. Manipulating the tilt and rotation of the catheter is commonly referred to as mechanical manipulation. Tilt and rotation manipulations may also be performed for the ultrasound imaging plane from the catheter which is referred to as electronical steering.

SUMMARY

Systems and methods for providing a multiplane suggested orientation by tracking a target are described. The systems and methods include a catheter for performing medical electrophysiology, and a graphical user interface (GUI) for monitoring the catheter, the GUI being used to maintain inclusion of the target in a display to a user of the catheter during medical electrophysiology. The catheter and GUI operate in combination to displaying, during the procedure, a tilt angle for causing the device to follow the target in the display, receiving, as an input, a rotation angle of a current plane of a view of the device, receiving, as input, a point of interest related to the target, calculating a new plane of the view of the device using a vector in an axis after rotation and a vector from a center point of the device to the target, and calculating the angles between the rotation angle of the current plane and an angle of the new plane to provide for motion of the device to maintain inclusion of the target in the display.

BRIEF DESCRIPTION OF THE DRAWINGS

A more detailed understanding may be had from the following description, given by way of example in conjunction with the accompanying drawings, wherein like reference numerals in the figures indicate like elements, and wherein.

DETAILED DESCRIPTION

Figure 1:
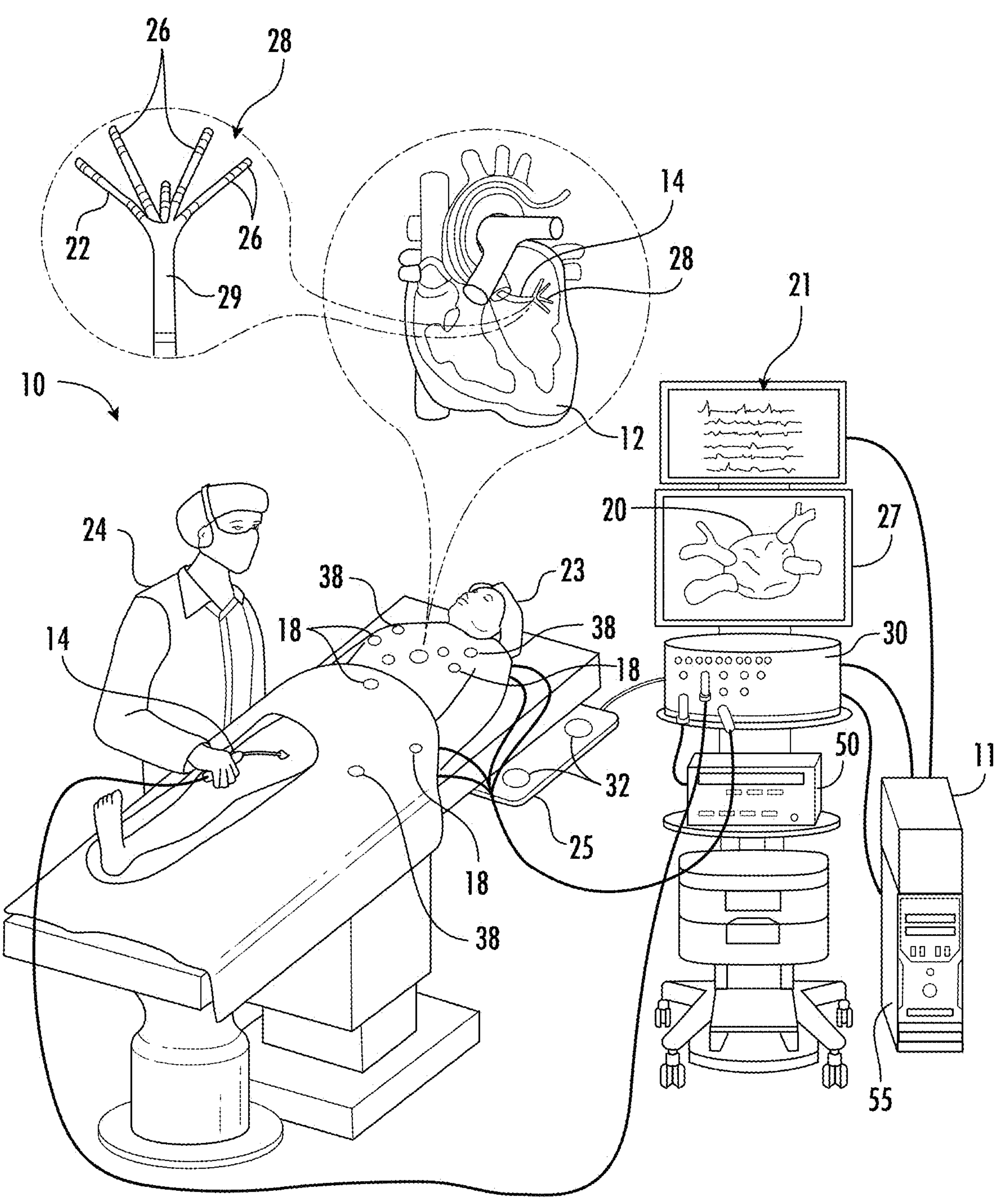
FIG. 1 depicts an example catheter-based electrophysiology mapping and ablation system according to one or more embodiments.

Systems and methods for providing a multiplane suggested orientation by tracking a target are described. The systems and methods include a catheter for performing medical electrophysiology, and a graphical user interface (GUI) for monitoring the catheter, the GUI being used to maintain inclusion of the target in a display to a user of the catheter during medical electrophysiology. The catheter and GUI operate in combination to displaying, during the procedure, a tilt angle for moving the device to follow the target in the display, receiving, as an input, a rotation angle of a current plane of a view of the device, receiving, as input, a point of interest related to the target, calculating a new plane of the view of the device using a vector in an axis after rotation and a vector from a center point of the device to the target, and calculating the angles between the rotation angle of the current plane and an angle of the new plane to provide for motion of the device to maintain inclusion of the target in the display.

A system and method for tracking a target to maintain inclusion of the target in a display for a user of a device during a procedure is also included. The system and method include displaying, during the procedure, a tilt angle for moving the device to follow the target in the display, receiving, as an input, a rotation angle of a current plane of a view of the device, receiving, as input, a point of interest related to the target, calculating a new plane of the view of the device using a vector in an axis after rotation and a vector from a center point of the device to the target, and calculating the angles between the rotation angle of the current plane and an angle of the new plane to provide for motion of the device to maintain inclusion of the target in the display.

A system and method for tracking a target and a direction of the target to maintain inclusion of the target in a display for a user of the device during a procedure is also included. The system and method include displaying, during the procedure, a tilt angle and a rotation angle for moving the device to follow the target in the display, receiving, as input, a device location, a point of interest related to the target, and a direction of the point of interest, calculating a normal of a plane represented by the direction of the point of interest and the device location, calculating new plane of a view of the device using a vector calculated from a cross-product between the calculated normal of the plane and a vector of the device, and the vector of the device, and calculating the angles between a current plane of the device represented by the normal of the plane and the calculated new plane of view of the device to maintain inclusion of the target in the display.

The systems and methods may use calculated angles that are multiplane and the multiplane represents the tilt and rotation of the device.

The systems and methods may further adjust the device to account for the calculated angles to render the new plane. The new plane may track the target in the display for the user of the device. The device may be a medical probe. The target may be a part of a patient body. The device may be a catheter and the target may be a pulmonary vein. The device may be four-dimensional catheter with views comprising dual plane mode, multi-plane mode and 4D.

In an example, a graphical user interface (GUI) may be provided. The GUI may provide a user a visible display for interacting with an imaging system, such as the CARTO system described herein. Specifically, the GUI may provide information to a user to guide the user on how to manipulate the catheter, such as the catheters described with respect to FIGS. 4A-4D below. This guide information may be based on the known location and orientation of the catheter, or another object of interest. The GUI may provide the tilt and/or the tilt and rotation value with associated direction in order to guide the user on the manipulation of the catheter to track the object of interest. Further, the present system may receive this guide information and manipulate the catheter to track the object of interest based on the guide information. In an example, arrows may be used to indicate the direction of the tilt and/or tilt and rotation of the catheter—to provide direction to increase or decrease, for example. The required tilt and rotation may be updated in real-time to accommodate for movement of the object of interest and/or the progression of the catheter within a portion of the object of interest. In this manner, the user can capture the slices that show the object of interest with high resolution.

Reference is made to FIG. 1 showing an example system (e.g., medical device equipment and/or catheter-based electrophysiology mapping and ablation system), shown as system 10, in which one or more features of the subject matter herein can be implemented according to one or more embodiments. All or part of the system 100 can be used to collect information (e.g., biometric data and/or a training dataset) and/or used to implement a machine learning and/or an artificial intelligence algorithm as described herein. The system 10, as illustrated, includes a recorder 11, a catheter 14, a model or anatomical map 20, an electrogram 21, a spline 22, a location pad 25, one or more electrodes 26, a display device 27, a distal tip 28, a sensor 29, a coil 32, a patient interface unit (PIU) 30, an electrode skin patches 38, an ablation energy generator 50, and a workstation 55. As would be understood, and as provided for a complete depiction, depicted with system 10 is a heart 12, a patient 23, and a physician 24 (which is representative of any medical professional, technician, or clinician). Each element and/or item of the system 10 is representative of one or more of that element and/or that item. The example of the system 10 shown in FIG. 1 can be modified to implement the embodiments disclosed herein. The disclosed embodiments can similarly be applied using other system components and settings. Additionally, the system 10 can include additional components, such as elements for sensing electrical activity, wired or wireless connectors, processing and display devices, or the like.

The system 10 includes multiple catheters 14, which are percutaneously inserted by the physician 24 through the patient's vascular system into a chamber or vascular structure of the heart 12. Typically, a delivery sheath catheter is inserted into the left or right atrium near a desired location in the heart 12. Thereafter, a plurality of catheters can be inserted into the delivery sheath catheter to arrive at the desired location. The plurality of catheters 14 may include catheters dedicated for sensing Intracardiac Electrogram (IEGM) signals, catheters dedicated for ablating, and/or catheters dedicated for both sensing and ablating. The example catheter 14 that is configured for sensing IEGM is illustrated herein. The physician 24 brings the distal tip 28 of the catheter 14 into contact with a heart wall for sensing a target site in the heart 12. For ablation, the physician 24 may similarly bring a distal end of an ablation catheter to a target site for ablating.

The catheter 14 is an exemplary catheter that includes at least one and preferably multiple electrodes 26 optionally distributed over a plurality of splines 22 at the distal tip 28 and configured to sense the IEGM signals. The catheter 14 may additionally include the sensor 29 embedded in or near the distal tip 28 for tracking position and orientation of the distal tip 28. Optionally and preferably, the position sensor 29 is a magnetic based position sensor including three magnetic coils for sensing three-dimensional (3D) position and orientation.

The sensor 29 (e.g., a position or a magnetic based position sensor) may be operated together with the location pad 25 including a plurality of magnetic coils 32 configured to generate magnetic fields in a predefined working volume. Real time position of the distal tip 28 of the catheter 14 may be tracked based on magnetic fields generated with the location pad 25 and sensed by the sensor 29. Details of the magnetic based position sensing technology are described in U.S. Pat. Nos. 5,5391,199; 5,443,489; 5,558,091; 6,172,499; 6,239,724; 6,332,089; 6,484,118; 6,618,612; 6,690,963; 6,788,967; 6,892,091.

The system 10 includes one or more electrode patches 38 positioned for skin contact on the patient 23 to establish location reference for the location pad 25 as well as impedance-based tracking of the electrodes 26. For impedance-based tracking, electrical current is directed toward the electrodes 26 and sensed at the patches 38 (e.g., electrode skin patches) so that the location of each electrode can be triangulated via the patches 38. Details of the impedance-based location tracking technology are described in U.S. Pat. Nos. 7,536,218; 7,756,576; 7,848,787; 7,869,865; and 8,456,182, which are incorporated herein by reference.

The recorder 11 displays the electrograms 21 captured with the electrodes 18 (e.g., body surface electrocardiogram (ECG) electrodes) and intracardiac electrograms (IEGM) captured with the electrodes 26 of the catheter 14. The recorder 11 may include pacing capability for pacing the heart rhythm and/or may be electrically connected to a standalone pacer.

The system 10 may include the ablation energy generator 50 that is adapted to conduct ablative energy to the one or more of electrodes 26 at the distal tip 28 of the catheter 14 configured for ablating. Energy produced by the ablation energy generator 50 may include, but is not limited to, radiofrequency (RF) energy or pulsed-field ablation (PFA) energy, including monopolar or bipolar high-voltage DC pulses as may be used to effect irreversible electroporation (IRE), or combinations thereof.

The PIU 30 is an interface configured to establish electrical communication between catheters, electrophysiological equipment, power supply and the workstation 55 for controlling operation of the system 10. Electrophysiological equipment of the system 10 may include for example, multiple catheters 14, the location pad 25, the body surface ECG electrodes 18, the electrode patches 38, the ablation energy generator 50, and the recorder 11. Optionally, the PIU 30 additionally includes processing capability for implementing real-time computations of location of the catheters and for performing ECG calculations.

The workstation 55 includes memory, processor unit with memory or storage with appropriate operating software loaded therein, and user interface capability. The workstation 55 may provide multiple functions, optionally including (1) modeling the endocardial anatomy in three-dimensions (3D) and rendering the model or anatomical map 20 for display on the display device 27, (2) displaying on the display device 27 activation sequences (or other data) compiled from recorded electrograms 21 in representative visual indicia or imagery superimposed on the rendered anatomical map 20, (3) displaying real-time location and orientation of multiple catheters within the heart chamber, and (5) displaying on the display device 27 sites of interest such as places where ablation energy has been applied. One commercial product embodying elements of the system 10 is available as the CARTO™ 3 System, available from Biosense Webster, Inc., 31A Technology Drive, Irvine, CA 92618.

For instance, the system 10 can be part of a cardiac mapping system (e.g., CARTO® system sold by Biosense Webster) that is configured to obtain biometric data (e.g., anatomical and electrical measurements of a patient's organ, such as the heart 12 and as described herein) and perform a cardiac ablation procedure. More particularly, treatments for cardiac conditions such as cardiac arrhythmia often require obtaining a detailed mapping of cardiac tissue, chambers, veins, arteries and/or electrical pathways. For example, a prerequisite for performing a catheter ablation (as described herein) successfully is that the cause of the cardiac arrhythmia is accurately located in a chamber of the heart 12. Such locating may be done via an electrophysiological investigation during which electrical potentials are detected spatially resolved with a mapping catheter (e.g., the catheter 14) introduced into the chamber of the heart 12. This electrophysiological investigation, the so-called electro-anatomical mapping, thus provides 3D mapping data which can be displayed on the display device 27. In many cases, the mapping function and a treatment function (e.g., ablation) are provided by a single catheter or group of catheters such that the mapping catheter also operates as a treatment (e.g., ablation) catheter at the same time.

Figure 2:
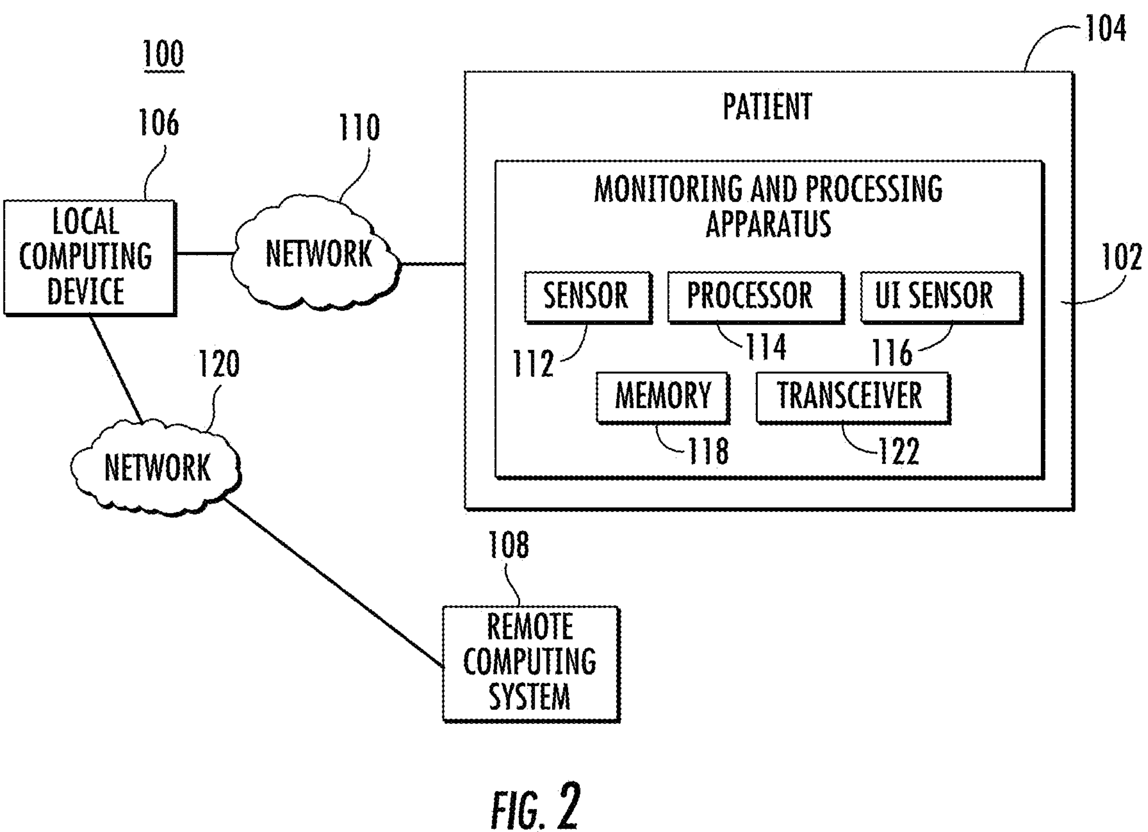
FIG. 2 is a block diagram of an example system for remotely monitoring and communicating patient biometrics according to one or more embodiments.

FIG. 2 is a block diagram of an example system 100 for remotely monitoring and communicating patient biometrics (i.e., patient data). In the example illustrated in FIG. 2, the system 100 includes a patient biometric monitoring and processing apparatus 102 associated with a patient 104, a local computing device 106, a remote computing system 108, a first network 110, a patient biometric sensor 112, a processor 114, a user input (UI) sensor 116, a memory 118, a second network 120, and a transmitter-receiver (i.e., transceiver) 122.

According to an example, the patient biometric monitoring and processing apparatus 102 may be an apparatus that is internal to the patient's body (e.g., subcutaneously implantable), such as the catheter 14 of FIG. 1. The patient biometric monitoring and processing apparatus 102 may be inserted into a patient via any applicable manner including orally injecting, surgical insertion via a vein or artery, an endoscopic procedure, or a laparoscopic procedure.

According to an example, the patient biometric monitoring and processing apparatus 102 may be an apparatus that is external to the patient, such as the electrode patches 38 of FIG. 1. For example, as described in more detail below, the patient biometric monitoring and processing apparatus 102 may include an attachable patch (e.g., that attaches to a patient's skin). The monitoring and processing apparatus 102 may also include a catheter with one or more electrodes, a probe, a blood pressure cuff, a weight scale, a bracelet or smart watch biometric tracker, a glucose monitor, a continuous positive airway pressure (CPAP) machine or virtually any device which may provide an input concerning the health or biometrics of the patient.

According to an example, the patient biometric monitoring and processing apparatus 102 may include both components that are internal to the patient and components that are external to the patient.

The single patient biometric monitoring and processing apparatus 102 is shown in FIG. 2. Example systems may, however, may include a plurality of patient biometric monitoring and processing apparatuses. A patient biometric monitoring and processing apparatus may be in communication with one or more other patient biometric monitoring and processing apparatuses. Additionally or alternatively, a patient biometric monitoring and processing apparatus may be in communication with the network 110.

One or more patient biometric monitoring and processing apparatuses 102 may acquire patient biometric data (e.g., electrical signals, blood pressure, temperature, blood glucose level or other biometric data) and receive at least a portion of the patient biometric data representing the acquired patient biometrics and additional formation associated with acquired patient biometrics from one or more other patient biometric monitoring and processing apparatuses 102. The additional information may be, for example, diagnosis information and/or additional information obtained from an additional device such as a wearable device. Each of the patient biometric monitoring and processing apparatus 102 may process data, including its own acquired patient biometrics as well as data received from one or more other patient biometric monitoring and processing apparatuses 102.

Biometric data (e.g., patient biometrics, patient data, or patient biometric data) can include one or more of local activation times (LATs), electrical activity, topology, bipolar mapping, reference activity, ventricle activity, dominant frequency, impedance, or the like. The LAT can be a point in time of a threshold activity corresponding to a local activation, calculated based on a normalized initial starting point. Electrical activity can be any applicable electrical signals that can be measured based on one or more thresholds and can be sensed and/or augmented based on signal to noise ratios and/or other filters. A topology can correspond to the physical structure of a body part or a portion of a body part and can correspond to changes in the physical structure relative to different parts of the body part or relative to different body parts. A dominant frequency can be a frequency, or a range of frequencies, that are prevalent at a portion of a body part and can be different in different portions of the same body part. For example, the dominant frequency of a PV of a heart can be different than the dominant frequency of the right atrium of the same heart. Impedance can be the resistance measurement at a given area of a body part.

Examples of biometric data include, but are not limited to, patient identification data, intracardiac electrocardiogram (IC ECG) data, bipolar intracardiac reference signals, anatomical and electrical measurements, trajectory information, body surface (BS) ECG data, historical data, brain biometrics, blood pressure data, ultrasound signals, radio signals, audio signals, a two- or three-dimensional image data, blood glucose data, and temperature data. The biometrics data can be used, generally, to monitor, diagnosis, and treatment any number of various diseases, such as cardiovascular diseases (e.g., arrhythmias, cardiomyopathy, and coronary artery disease) and autoimmune diseases (e.g., type I and type II diabetes). Note that BS ECG data can include data and signals collected from electrodes on a surface of a patient, IC ECG data can include data and signals collected from electrodes within the patient, and ablation data can include data and signals collected from tissue that has been ablated. Further, BS ECG data, IC ECG data, and ablation data, along with catheter electrode position data, can be derived from one or more procedure recordings.

In FIG. 2, the network 110 is an example of a short-range network (e.g., local area network (LAN), or personal area network (PAN)). Information may be sent, via the network 110, between the patient biometric monitoring and processing apparatus 102 and the local computing device 106 using any one of various short-range wireless communication protocols, such as Bluetooth, Wi-Fi, Zigbee, Z-Wave, near field communications (NFC), ultraband, Zigbee, or infrared (IR).

The network 120 may be a wired network, a wireless network or include one or more wired and wireless networks. For example, the network 120 may be a long-range network (e.g., wide area network (WAN), the internet, or a cellular network). Information may be sent, via the network 120 using any one of various long-range wireless communication protocols (e.g., TCP/IP, HTTP, 3G, 4G/LTE, or 5G/New Radio).

The patient biometric monitoring and processing apparatus 102 may include the patient biometric sensor 112, the processor 114, the UI sensor 116, the memory 118, and the transceiver 122. The patient biometric monitoring and processing apparatus 102 may continually or periodically monitor, store, process and communicate, via the network 110, any number of various patient biometrics. Examples of patient biometrics include electrical signals (e.g., ECG signals and brain biometrics), blood pressure data, blood glucose data and temperature data. The patient biometrics may be monitored and communicated for treatment across any number of various diseases, such as cardiovascular diseases (e.g., arrhythmias, cardiomyopathy, and coronary artery disease) and autoimmune diseases (e.g., type I and type II diabetes).

The patient biometric sensor 112 may include, for example, one or more sensors configured to sense a type of biometric patient biometrics. For example, the patient biometric sensor 112 may include an electrode configured to acquire electrical signals (e.g., heart signals, brain signals or other bioelectrical signals), a temperature sensor, a blood pressure sensor, a blood glucose sensor, a blood oxygen sensor, a pH sensor, an accelerometer and a microphone.

As described in more detail below, the patient biometric monitoring and processing apparatus 102 may be an ECG monitor for monitoring ECG signals of a heart (e.g., the heart 12). The patient biometric sensor 112 of the ECG monitor may include one or more electrodes for acquiring ECG signals. The ECG signals may be used for treatment of various cardiovascular diseases.

In another example, the patient biometric monitoring and processing apparatus 102 may be a continuous glucose monitor (CGM) for continuously monitoring blood glucose levels of a patient on a continual basis for treatment of various diseases, such as type I and type II diabetes. The CGM may include a subcutaneously disposed electrode, which may monitor blood glucose levels from interstitial fluid of the patient. The CGM may be, for example, a component of a closed-loop system in which the blood glucose data is sent to an insulin pump for calculated delivery of insulin without user intervention.

The transceiver 122 may include a separate transmitter and receiver. Alternatively, the transceiver 122 may include a transmitter and receiver integrated into a single device.

The processor 114 may be configured to store patient data, such as patient biometric data in the memory 118 acquired by the patient biometric sensor 112, and communicate the patient data, across the network 110, via a transmitter of the transceiver 122. Data from one or more other patient biometric monitoring and processing apparatus 102 may also be received by a receiver of the transceiver 122, as described in more detail below.

According to an example, the patient biometric monitoring and processing apparatus 102 includes UI sensor 116 which may be, for example, a piezoelectric sensor or a capacitive sensor configured to receive a user input, such as a tapping or touching. For example, the UI sensor 116 may be controlled to implement a capacitive coupling, in response to tapping or touching a surface of the patient biometric monitoring and processing apparatus 102 by the patient 104. Gesture recognition may be implemented via any one of various capacitive types, such as resistive capacitive, surface capacitive, projected capacitive, surface acoustic wave, piezoelectric and infra-red touching. Capacitive sensors may be disposed at a small area or over a length of the surface such that the tapping or touching of the surface activates the monitoring device.

As described in more detail below, the processor 114 may be configured to respond selectively to different tapping patterns of the capacitive sensor (e.g., a single tap or a double tap), which may be the UI sensor 116, such that different tasks of the patch (e.g., acquisition, storing, or transmission of data) may be activated based on the detected pattern. In some embodiments, audible feedback may be given to the user from the patient biometric monitoring and processing apparatus 102 when a gesture is detected.

The local computing device 106 of the system 100 is in communication with the patient biometric monitoring and processing apparatus 102 and may be configured to act as a gateway to the remote computing system 108 through the second network 120. The local computing device 106 may be, for example, a, smart phone, smartwatch, tablet or other portable smart device configured to communicate with other devices via the network 120. Alternatively, the local computing device 106 may be a stationary or standalone device, such as a stationary base station including, for example, modem and/or router capability, a desktop or laptop computer using an executable program to communicate information between the patient biometric monitoring and processing apparatus 102 and the remote computing system 108 via the PC's radio module, or a USB dongle. Patient biometrics may be communicated between the local computing device 106 and the patient biometric monitoring and processing apparatus 102 using a short-range wireless technology standard (e.g., Bluetooth, Wi-Fi, ZigBee, Z-wave and other short-range wireless standards) via the short-range wireless network 110, such as a local area network (LAN) (e.g., a personal area network (PAN)). In some embodiments, the local computing device 106 may also be configured to display the acquired patient electrical signals and information associated with the acquired patient electrical signals, as described in more detail below.

In some embodiments, the remote computing system 108 may be configured to receive at least one of the monitored patient biometrics and information associated with the monitored patient via network 120, which is a long-range network. For example, if the local computing device 106 is a mobile phone, network 120 may be a wireless cellular network, and information may be communicated between the local computing device 106 and the remote computing system 108 via a wireless technology standard, such as any of the wireless technologies mentioned above. As described in more detail below, the remote computing system 108 may be configured to provide (e.g., visually display and/or aurally provide) the at least one of the patient biometrics and the associated information to a healthcare professional (e.g., a physician).

Figure 3:
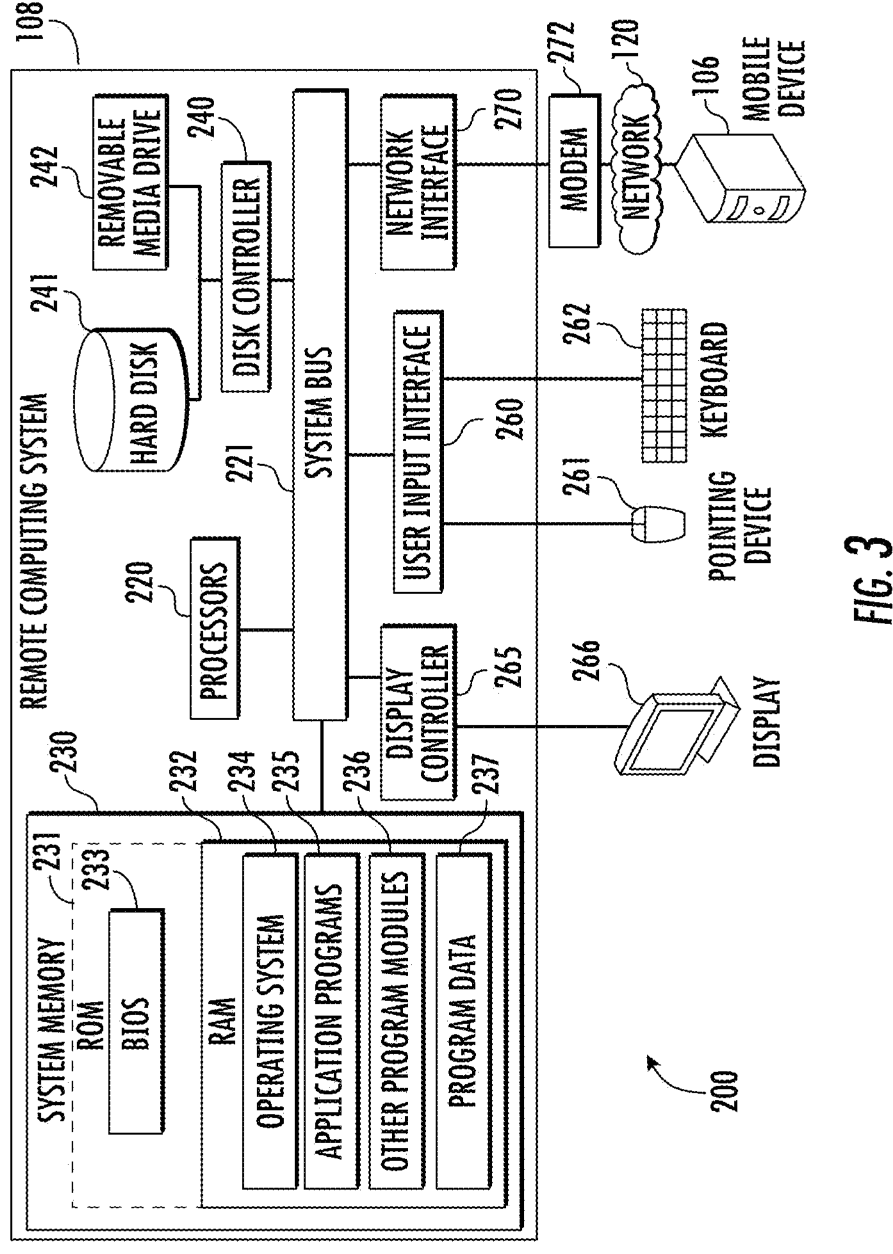
FIG. 3 is a system diagram of an example of a computing environment in communication with network according to one or more embodiments.

FIG. 3 is a system diagram of an example of a computing environment 200 in communication with network 120. In some instances, the computing environment 200 is incorporated in a public cloud computing platform (such as Amazon Web Services or Microsoft Azure), a hybrid cloud computing platform (such as HP Enterprise OneSphere) or a private cloud computing platform.

As shown in FIG. 3, computing environment 200 includes remote computing system 108 (hereinafter computer system), which is one example of a computing system upon which embodiments described herein may be implemented.

The remote computing system 108 may, via processors 220, which may include one or more processors, perform various functions. The functions may include analyzing monitored patient biometrics and the associated information and, according to physician-determined or algorithm driven thresholds and parameters, providing (e.g., via display 266) alerts, additional information or instructions. As described in more detail below, the remote computing system 108 may be used to provide (e.g., via display 266) healthcare personnel (e.g., a physician) with a dashboard of patient information, such that such information may enable healthcare personnel to identify and prioritize patients having more critical needs than others.

As shown in FIG. 3, the computer system 210 may include a communication mechanism such as a bus 221 or other communication mechanism for communicating information within the computer system 210. The computer system 210 further includes one or more processors 220 coupled with the bus 221 for processing the information. The processors 220 may include one or more CPUs, GPUs, or any other processor known in the art.

The computer system 210 also includes a system memory 230 coupled to the bus 221 for storing information and instructions to be executed by processors 220. The system memory 230 may include computer readable storage media in the form of volatile and/or nonvolatile memory, such as read only system memory (ROM) 231 and/or random-access memory (RAM) 232. The system memory RAM 232 may include other dynamic storage device(s) (e.g., dynamic RAM, static RAM, and synchronous DRAM). The system memory ROM 231 may include other static storage device (s) (e.g., programmable ROM, erasable PROM, and electrically erasable PROM). In addition, the system memory 230 may be used for storing temporary variables or other intermediate information during the execution of instructions by the processors 220. A basic input/output system 233 (BIOS) may contain routines to transfer information between elements within computer system 210, such as during start-up, that may be stored in system memory ROM 231. RAM 232 may comprise data and/or program modules that are immediately accessible to and/or presently being operated on by the processors 220. System memory 230 may additionally include, for example, operating system 234, application programs 235, other program modules 236 and program data 237.

The illustrated computer system 210 also includes a disk controller 240 coupled to the bus 221 to control one or more storage devices for storing information and instructions, such as a magnetic hard disk 241 and a removable media drive 242 (e.g., floppy disk drive, compact disc drive, tape drive, and/or solid-state drive). The storage devices may be added to the computer system 210 using an appropriate device interface (e.g., a small computer system interface (SCSI), integrated device electronics (IDE), Universal Serial Bus (USB), or FireWire).

The computer system 210 may also include a display controller 265 coupled to the bus 221 to control a monitor or display 266, such as a cathode ray tube (CRT) or liquid crystal display (LCD), for displaying information to a computer user. The illustrated computer system 210 includes a user input interface 260 and one or more input devices, such as a keyboard 262 and a pointing device 261, for interacting with a computer user and providing information to the processor 220. The pointing device 261, for example, may be a mouse, a trackball, or a pointing stick for communicating direction information and command selections to the processor 220 and for controlling cursor movement on the display 266. The display 266 may provide a touch screen interface that may allow input to supplement or replace the communication of direction information and command selections by the pointing device 261 and/or keyboard 262.

The computer system 210 may perform a portion or each of the functions and methods described herein in response to the processors 220 executing one or more sequences of one or more instructions contained in a memory, such as the system memory 230. Such instructions may be read into the system memory 230 from another computer readable medium, such as a hard disk 241 or a removable media drive 242. The hard disk 241 may contain one or more data stores and data files used by embodiments described herein. Data store contents and data files may be encrypted to improve security. The processors 220 may also be employed in a multi-processing arrangement to execute the one or more sequences of instructions contained in system memory 230. In alternative embodiments, hard-wired circuitry may be used in place of or in combination with software instructions. Thus, embodiments are not limited to any specific combination of hardware circuitry and software.

As stated above, the computer system 210 may include at least one computer readable medium or memory for holding instructions programmed according to embodiments described herein and for containing data structures, tables, records, or other data described herein. The term computer readable medium as used herein refers to any non-transitory, tangible medium that participates in providing instructions to the processor 220 for execution. A computer readable medium may take many forms including, but not limited to, non-volatile media, volatile media, and transmission media. Non-limiting examples of non-volatile media include optical disks, solid state drives, magnetic disks, and magneto-optical disks, such as hard disk 241 or removable media drive 242. Non-limiting examples of volatile media include dynamic memory, such as system memory 230. Non-limiting examples of transmission media include coaxial cables, copper wire, and fiber optics, including the wires that make up the bus 221. Transmission media may also take the form of acoustic or light waves, such as those generated during radio wave and infrared data communications.

The computing environment 200 may further include the computer system 210 operating in a networked environment using logical connections to local computing device 106 and one or more other devices, such as a personal computer (laptop or desktop), mobile devices (e.g., patient mobile devices), a server, a router, a network PC, a peer device or other common network node, and typically includes many or all of the elements described above relative to computer system 210. When used in a networking environment, computer system 210 may include modem 272 for establishing communications over a network 120, such as the Internet. Modem 272 may be connected to system bus 221 via network interface 270, or via another appropriate mechanism.

Network 120, as shown in FIGS. 2 and 3, may be any network or system generally known in the art, including the Internet, an intranet, a local area network (LAN), a wide area network (WAN), a metropolitan area network (MAN), a direct connection or series of connections, a cellular telephone network, or any other network or medium capable of facilitating communication between computer system 610 and other computers (e.g., local computing device 106).

Treatments for cardiac conditions such as cardiac arrhythmia often require obtaining a detailed mapping of cardiac tissue, chambers, veins, arteries and/or electrical pathways. For example, a prerequisite for performing a catheter ablation successfully is that the cause of the cardiac arrhythmia is accurately located in the heart chamber. Such locating may be done via an electrophysiological investigation during which electrical potentials are detected and spatially resolved with a mapping catheter introduced into the heart chamber. This electrophysiological investigation, the so-called electro-anatomical mapping, thus provides 3D mapping data which can be displayed on a monitor. In many cases, the mapping function and a treatment function (e.g., ablation) are provided by a single catheter or group of catheters such that the mapping catheter also operates as a treatment (e.g., ablation) catheter at the same time Mapping of cardiac areas such as cardiac regions, tissue, veins, arteries and/or electrical pathways of the heart may result in identifying problem areas such as scar tissue, arrythmia sources (e.g., electric rotors), healthy areas, and the like. Cardiac areas may be mapped such that a visual rendering of the mapped cardiac areas is provided using a display, as further disclosed herein. Additionally, cardiac mapping may include mapping based on one or more modalities such as, but not limited to local activation time (LAT), an electrical activity, a topology, a bipolar mapping, a dominant frequency, or an impedance. Data corresponding to multiple modalities may be captured using a catheter inserted into a patient's body and may be provided for rendering at the same time or at different times based on corresponding settings and/or preferences of a medical professional.

Cardiac mapping may be implemented using one or more techniques. As an example of a technique, cardiac mapping may be implemented by sensing an electrical property of heart tissue, for example, local activation time, as a function of the precise location within the heart. The corresponding data may be acquired with one or more catheters that are advanced into the heart using catheters that have electrical and location sensors in their distal tips. As specific examples, location and electrical activity may be initially measured on about 10 to about 20 points on the interior surface of the heart. These data points may be generally sufficient to generate a preliminary reconstruction or map of the cardiac surface to a satisfactory quality. The preliminary map may be combined with data taken at additional points in order to generate a more comprehensive map of the heart's electrical activity. In clinical settings, it is not uncommon to accumulate data at 100 or more sites to generate a detailed, comprehensive map of heart chamber electrical activity. The generated detailed map may then serve as the basis for deciding on a therapeutic course of action, for example, tissue ablation, to alter the propagation of the heart's electrical activity and to restore normal heart rhythm.

Catheters containing position sensors may be used to determine the trajectory of points on the cardiac surface. These trajectories may be used to infer motion characteristics such as the contractility of the tissue. Maps depicting such motion characteristics may be constructed when the trajectory information is sampled at a sufficient number of points in the heart.

Electrical activity at a point in the heart may be typically measured by advancing a catheter containing an electrical sensor at or near its distal tip to a specific point in the heart, contacting the tissue with the sensor and acquiring data at that point. One drawback with mapping a cardiac chamber using a catheter containing only a single, distal tip electrode is the long period of time required to accumulate data on a point-by-point basis over the requisite number of points required for a detailed map of the chamber as a whole. Accordingly, multiple-electrode and high-density mapping catheters have been developed to simultaneously measure electrical activity at multiple points in the heart chamber.

Figure 4A:
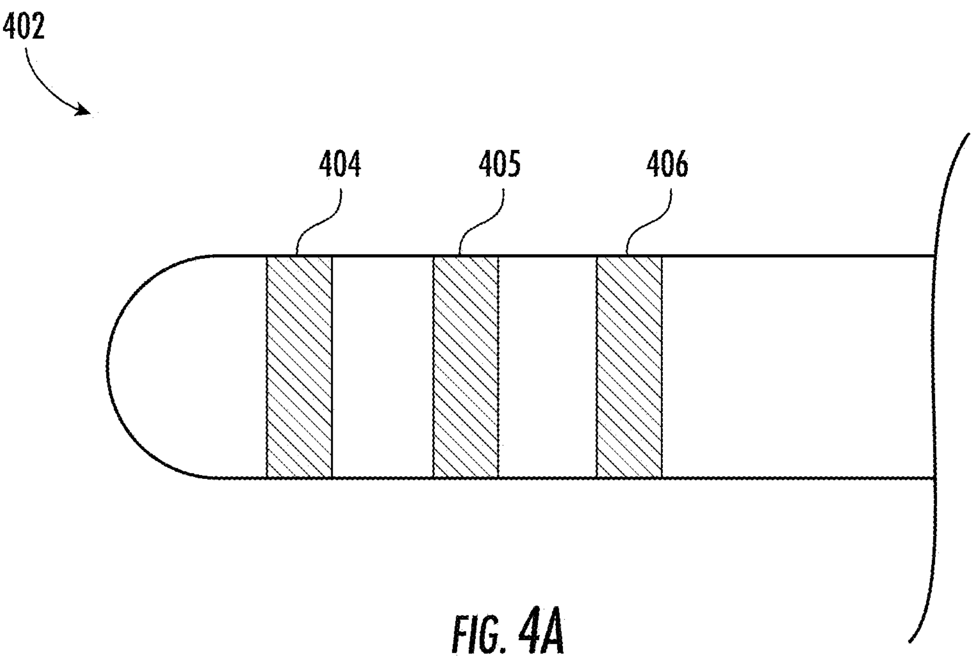
FIG. 4A shows an example of a linear catheter including multiple electrodes that may be used to map a cardiac area.

Multiple-electrode catheters may be implemented using any applicable shape such as a linear catheter with multiple electrodes, a balloon catheter including electrodes dispersed on multiple spines that shape the balloon, a lasso or loop catheter with multiple electrodes, or any other applicable shape. FIG. 4A shows an example of a linear catheter 402 including multiple electrodes 404, 405, and 406 that may be used to map a cardiac area. Linear catheter 402 may be fully or partially elastic such that it can twist, bend, and or otherwise change its shape based on received signal and/or based on application of an external force (e.g., cardiac tissue) on the linear catheter 402.

Figure 4B:
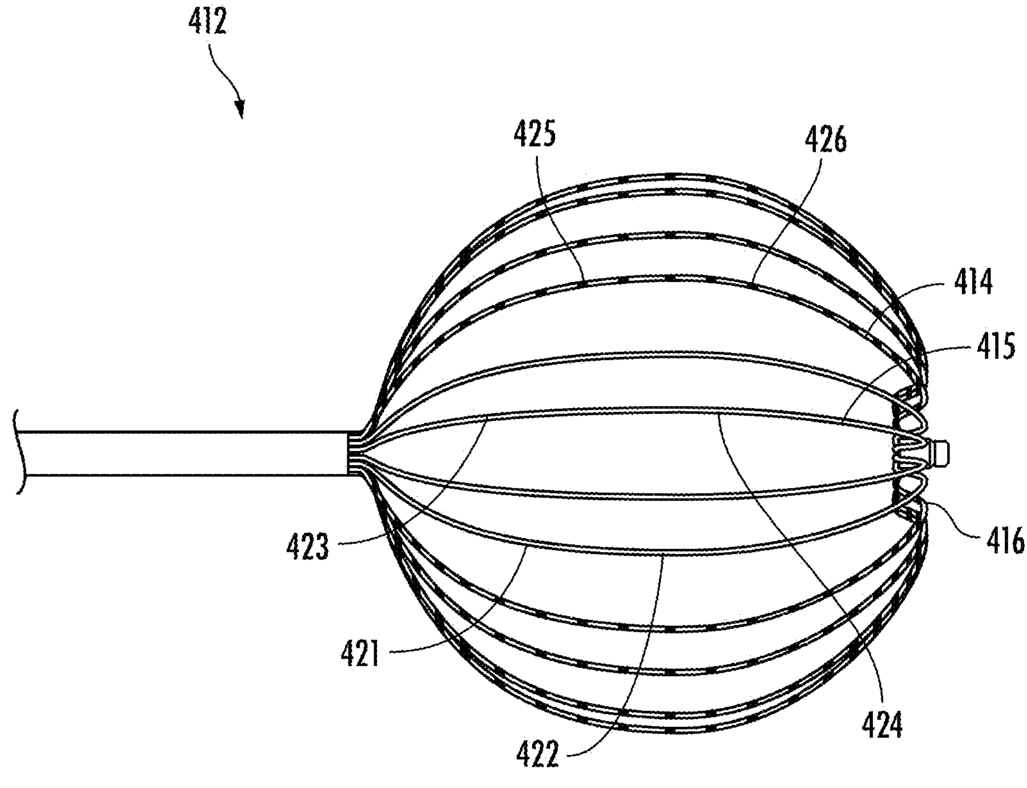
FIG. 4B shows an example of a balloon catheter including multiple splines and multiple electrodes on each spline.

FIG. 4B shows an example of a balloon catheter 412 including multiple splines (e.g., 12 splines in the specific example of FIG. 4B) including splines 414, 416, 417 and multiple electrodes on each spline including electrodes 421, 422, 423, 424, 425, and 426 as shown. The balloon catheter 412 may be designed such that when deployed into a patient's body, its electrodes may be held in intimate contact against an endocardial surface. As an example, a balloon catheter may be inserted into a lumen, such as a pulmonary vein (PV). The balloon catheter may be inserted into the PV in a deflated state such that the balloon catheter does not occupy its maximum volume while being inserted into the PV. The balloon catheter may expand while inside the PV such that electrodes on the balloon catheter are in contact with an entire circular section of the PV. Such contact with an entire circular section of the PV, or any other lumen, may enable efficient mapping and/or ablation.

Figure 4C:
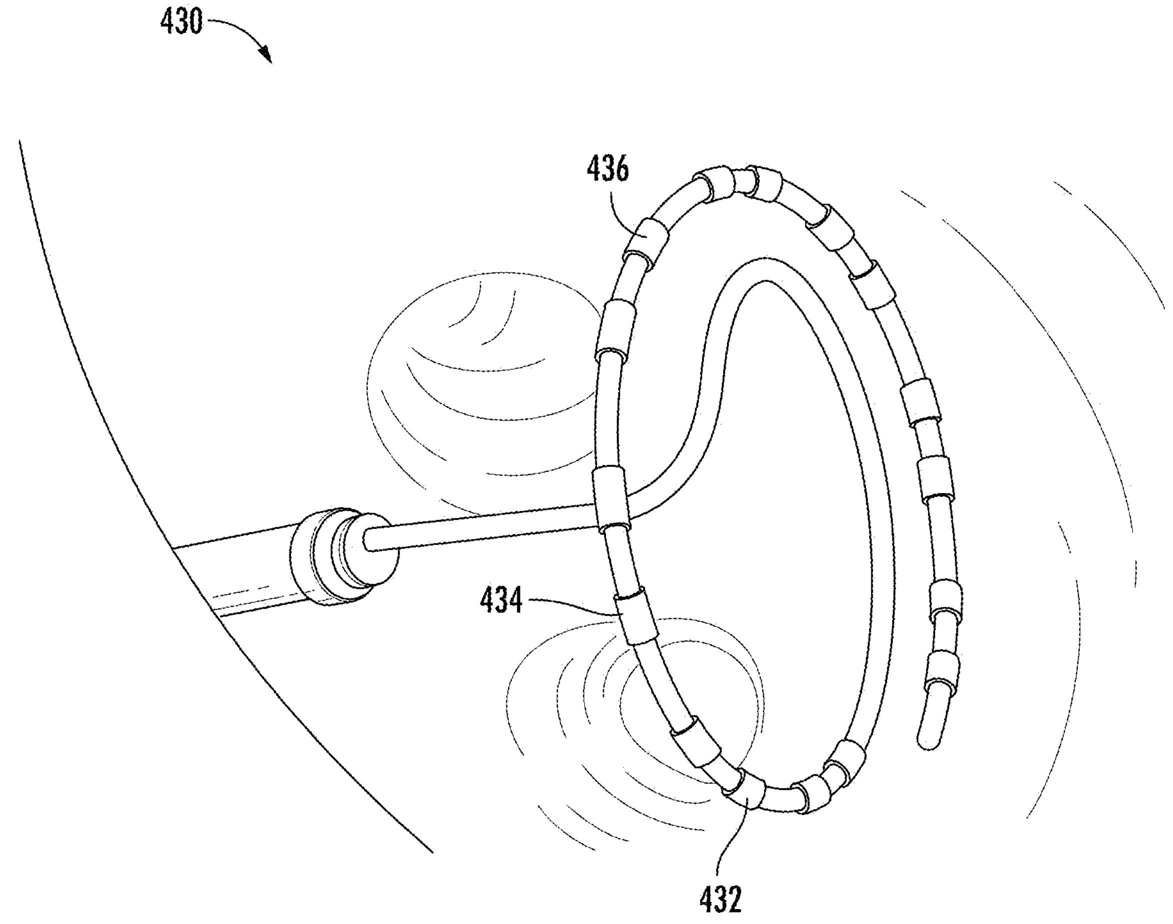
FIG. 4C shows an example of a loop catheter including multiple electrodes that may be used to map a cardiac area.

FIG. 4C shows an example of a loop catheter 430 (also referred to as a lasso catheter) including multiple electrodes 432, 434, and 436 that may be used to map a cardiac area. Loop catheter 430 may be fully or partially elastic such that it can twist, bend, and or otherwise change its shape based on received signal and/or based on application of an external force (e.g., cardiac tissue) on the loop catheter 430.

Figure 4D:
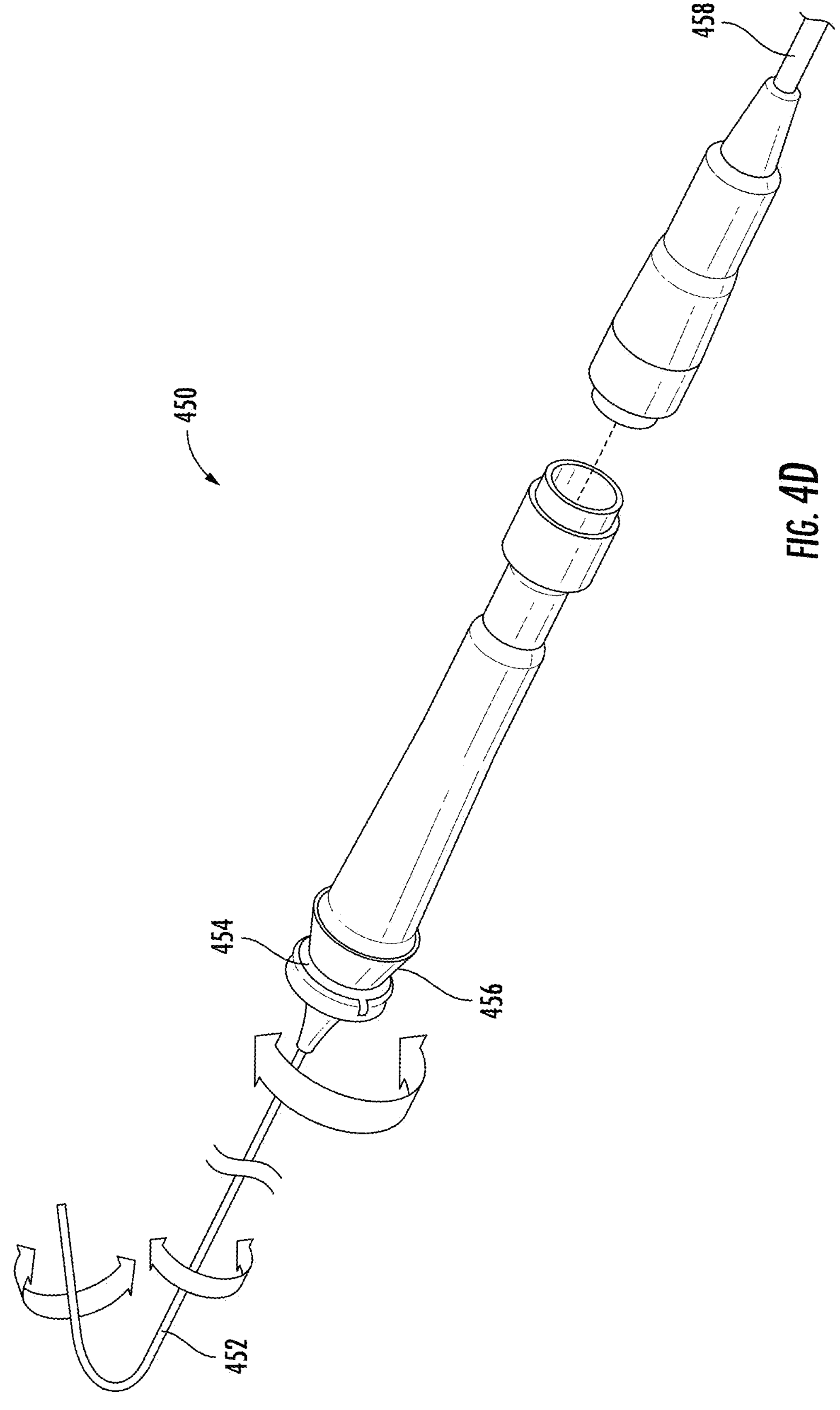
FIG. 4D shows an example of an intracardiac echocardiogram (ICE) catheter that is capable of providing real-time, three-dimensional visualizations of the interior of the heart.

FIG. 4D shows an example of an intracardiac echocardiogram (ICE) catheter 450 that is capable of providing real-time, three-dimensional visualizations of the interior of the heart. ICE catheter 450 includes a torqueable and deflectable shaft 452 that provides for extension and rotation of the transducer. ICE catheter 450 includes transducer orientation adjustment 454 and a shaft deflector 456, as well as connector cable 458. ICE catheter 450 is capable of providing a 4D intracardiac echocardiogram with a field of view of 90 degrees×90 degrees. ICE catheter 450 may include independent rotation and extension via shaft 452 and adjustment 454.

According to an example, a multi-electrode catheter may be advanced into a chamber of the heart. Anteroposterior (AP) and lateral fluorograms may be obtained to establish the position and orientation of each of the electrodes. Electrograms may be recorded from each of the electrodes in contact with a cardiac surface relative to a temporal reference such as the onset of the P-wave in sinus rhythm from a body surface ECG. The system, as further disclosed herein, may differentiate between those electrodes that register electrical activity and those that do not due to absence of close proximity to the endocardial wall. After initial electrograms are recorded, the catheter may be repositioned, and fluorograms and electrograms may be recorded again. An electrical map may then be constructed from iterations of the process above.

According to an example, cardiac mapping may be generated based on detection of intracardiac electrical potential fields. A non-contact technique to simultaneously acquire a large amount of cardiac electrical information may be implemented. For example, a catheter having a distal end portion may be provided with a series of sensor electrodes distributed over its surface and connected to insulated electrical conductors for connection to signal sensing and processing means. The size and shape of the end portion may be such that the electrodes are spaced substantially away from the wall of the cardiac chamber. Intracardiac potential fields may be detected during a single cardiac beat. According to an example, the sensor electrodes may be distributed on a series of circumferences lying in planes spaced from each other. These planes may be perpendicular to the major axis of the end portion of the catheter. At least two additional electrodes may be provided adjacent at the ends of the major axis of the end portion. As a more specific example, the catheter may include four circumferences with eight electrodes spaced equiangularly on each circumference. Accordingly, in this specific implementation, the catheter may include at least 34 electrodes (32 circumferential and 2 end electrodes).

According to another example, an electrophysiological cardiac mapping system and technique based on a non-contact and non-expanded multi-electrode catheter may be implemented. Electrograms may be obtained with catheters having multiple electrodes (e.g., between 42 to 122 electrodes). According to an example, knowledge of the relative geometry of the probe and the endocardium may be obtained such as by an independent imaging modality such as transesophogeal echocardiography. After the independent imaging, non-contact electrodes may be used to measure cardiac surface potentials and construct maps therefrom. This technique may include the following steps (after the independent imaging step): (a) measuring electrical potentials with a plurality of electrodes disposed on a probe positioned in the heart; (b) determining the geometric relationship of the probe surface and the endocardial surface; (c) generating a matrix of coefficients representing the geometric relationship of the probe surface and the endocardial surface; and (d) determining endocardial potentials based on the electrode potentials and the matrix of coefficients.

According to an example, a technique and apparatus for mapping the electrical potential distribution of a heart chamber may be implemented. An intra-cardiac multielectrode mapping catheter assembly may be inserted into a patient's heart. The mapping catheter assembly may include a multi-electrode array with an integral reference electrode, or, preferably, a companion reference catheter. The electrodes may be deployed in the form of a substantially spherical array. The electrode array may be spatially referenced to a point on the endocardial surface by the reference electrode or by the reference catheter which is brought into contact with the endocardial surface. The preferred electrode array catheter may carry a number of individual electrode sites (e.g., at least 24). Additionally, this example technique may be implemented with knowledge of the location of each of the electrode sites on the array, as well as a knowledge of the cardiac geometry. These locations are preferably determined by a technique of impedance plethysmography.

According to an example, a heart mapping catheter assembly may include an electrode array defining a number of electrode sites. The mapping catheter assembly may also include a lumen to accept a reference catheter having a distal tip electrode assembly which may be used to probe the heart wall. The mapping catheter may include a braid of insulated wires (e.g., having 24 to 64 wires in the braid), and each of the wires may be used to form electrode sites. The catheter may be readily positionable in a heart to be used to acquire electrical activity information from a first set of non-contact electrode sites and/or a second set of in-contact electrode sites.

According to an example, another catheter for mapping electrophysiological activity within the heart may be implemented. The catheter body may include a distal tip which is adapted for delivery of a stimulating pulse for pacing the heart or an ablative electrode for ablating tissue in contact with the tip. The catheter may further include at least one pair of orthogonal electrodes to generate a difference signal indicative of the local cardiac electrical activity adjacent the orthogonal electrodes.

According to an example, a process for measuring electrophysiologic data in a heart chamber may be implemented. The method may include, in part, positioning a set of active and passive electrodes into the heart, supplying current to the active electrodes, thereby generating an electric field in the heart chamber, and measuring the electric field at the passive electrode sites. The passive electrodes are contained in an array positioned on an inflatable balloon of a balloon catheter. In preferred embodiments, the array is said to have from 60 to 64 electrodes.

According to an example, cardiac imaging may be implemented using one or more ultrasound transducers. The ultrasound transducers may be inserted into a patient's heart and may collect a plurality of ultrasound slices (e.g., two dimensional or three-dimensional slices, sometimes referred to as wedges or volumes) at various locations and orientations within the heart. The location and orientation of a given ultrasound transducer may be known and the collected ultrasound slices may be stored such that they can be displayed at a later time. One or more ultrasound slices corresponding to the position of a probe (e.g., a treatment catheter) at the later time may be displayed and the probe may be overlaid onto the one or more ultrasound slices.

According to other examples, body patches and/or body surface electrodes may be positioned on or proximate to a patient's body. A catheter with one or more electrodes may be positioned within the patient's body (e.g., within the patient's heart) and the position of the catheter may be determined by a system based on signals transmitted and received between the one or more electrodes of the catheter and the body patches and/or body surface electrodes. Additionally, the catheter electrodes may sense biometric data (e.g., LAT values) from within the body of the patient (e.g., within the heart). The biometric data may be associated with the determined position of the catheter such that a rendering of the patient's body part (e.g., heart) may be displayed and may show the biometric data overlaid on a shape of the body part, as determined by the position of the catheter. 4D ICE systems may include viewing modes that include dual-plane mode, multi-plane mode and 4D. The dual mode/multi-plane modes generally provide higher resolution 2D images as compared to 2D images extracted from the 4D mode.

In an example, a graphical user interface (GUI) may be provided. The GUI may provide a user a visible display for interacting with the cardiac mapping system such as the example systems described above. Specifically, the GUI may provide information to a user to guide the user on how to manipulate the catheter, such as the catheters described above with respect to FIGS. 4A-4D. This information may be based on the known location and orientation of the catheter or another object of interest. The GUI may provide the tilt and/or the tilt and rotation value with associated direction in order to guide the user on the manipulation of the catheter to change and adjust the tilt and rotation angles of the field of view or fan displayed from the catheter. Further, the present system may receive this information and manipulate the catheter based on the information. In an example, arrows may be used to indicate the direction of the tilt and/or tilt and rotation of the fan displayed from the catheter—to provide direction to increase or decrease, for example. The required tilt and rotation may be updated in real-time to accommodate for movement of the object of interest. In this manner, the user can capture the slices that show the object of interest with high resolution.

Figure 5:
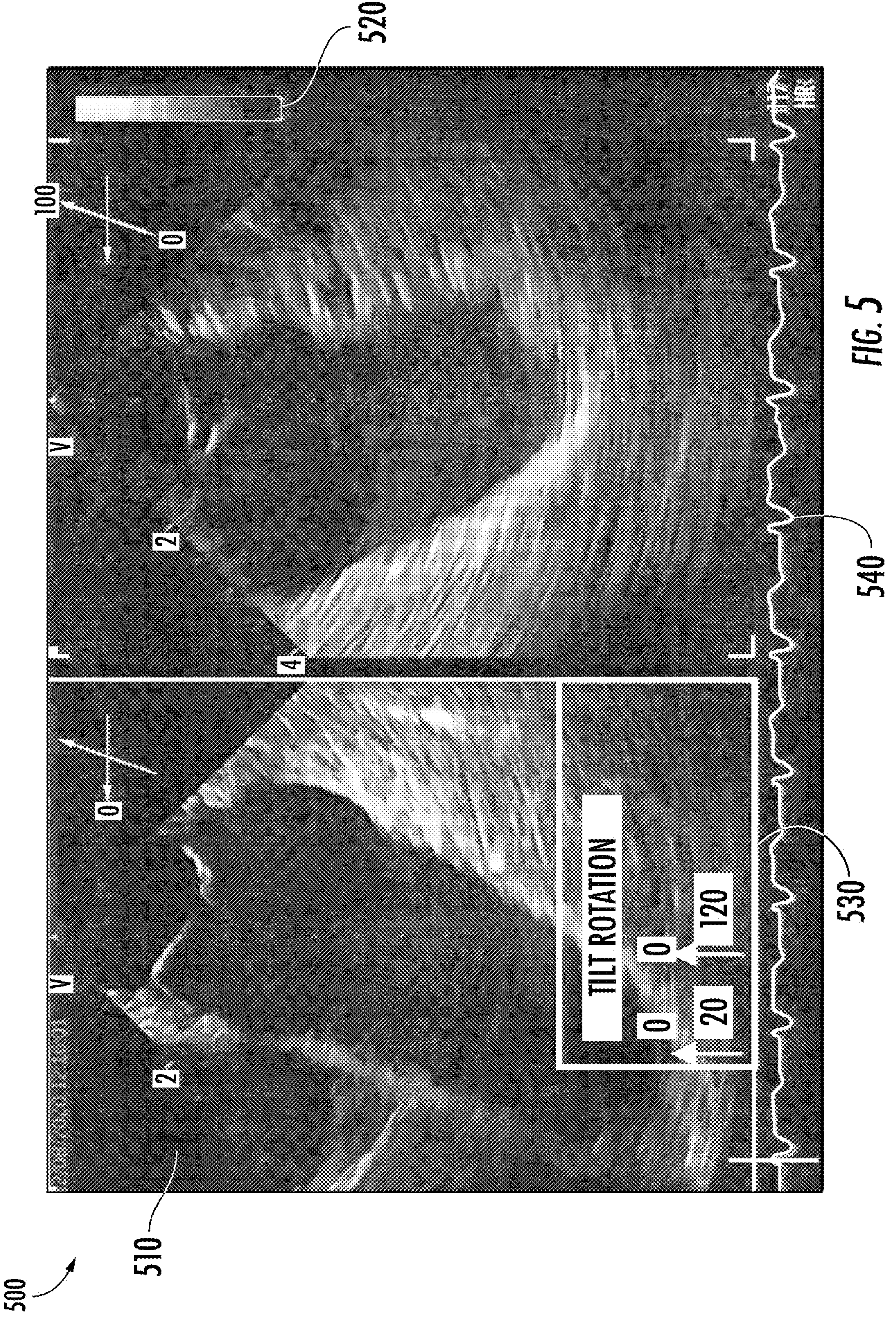
FIG. 5 illustrates a graphical user interface (GUI) configured to provide the tilt and rotation needed to track an object of interest.

FIG. 5 illustrates a graphical user interface (GUI) 500 configured to provide the tilt and rotation needed to track an object of interest. As illustrated GUI 500 may include a first view window 510 and a second view window 520. In tracking a point of interest, GUI 500 may provide guidance as to the tilt and rotation angles to adjust to view the point of interest. The guidance tilt and rotation angles may be provided within a window 530. Window 530 may be displayed as an overlay window overlaying one or both of first view window 510 and second view window 520. Additionally, information associated with the measurements that are being performed may be included. As depicted in FIG. 5, a heart rate 540 may be provided in signal form. The average heart may additional be displayed. As set forth herein, the location of any element may be tracked. The present examples are directed to an ablation catheter, by way of example only.

In an example, the system may know or define the location of an ablation catheter and provide a depiction of the ablation catheter within first view window 510 from a first vantage point, and within second view window 520 from a second vantage point. The first and second vantage points may be orthogonal to one another to provide the best viewing for a user of the ablation catheter. Upon movement of the ablation catheter, it may move from within the first view window 510 and/or the second view window 520. In this example, a tilt angle and a rotation angle may be displayed in window 530. The tilt angle and rotation angle may each be calculated as described below and may be configured to maintain the view of the ablation catheter within the first view window 510 and/or the second view window.

Figure 6A:
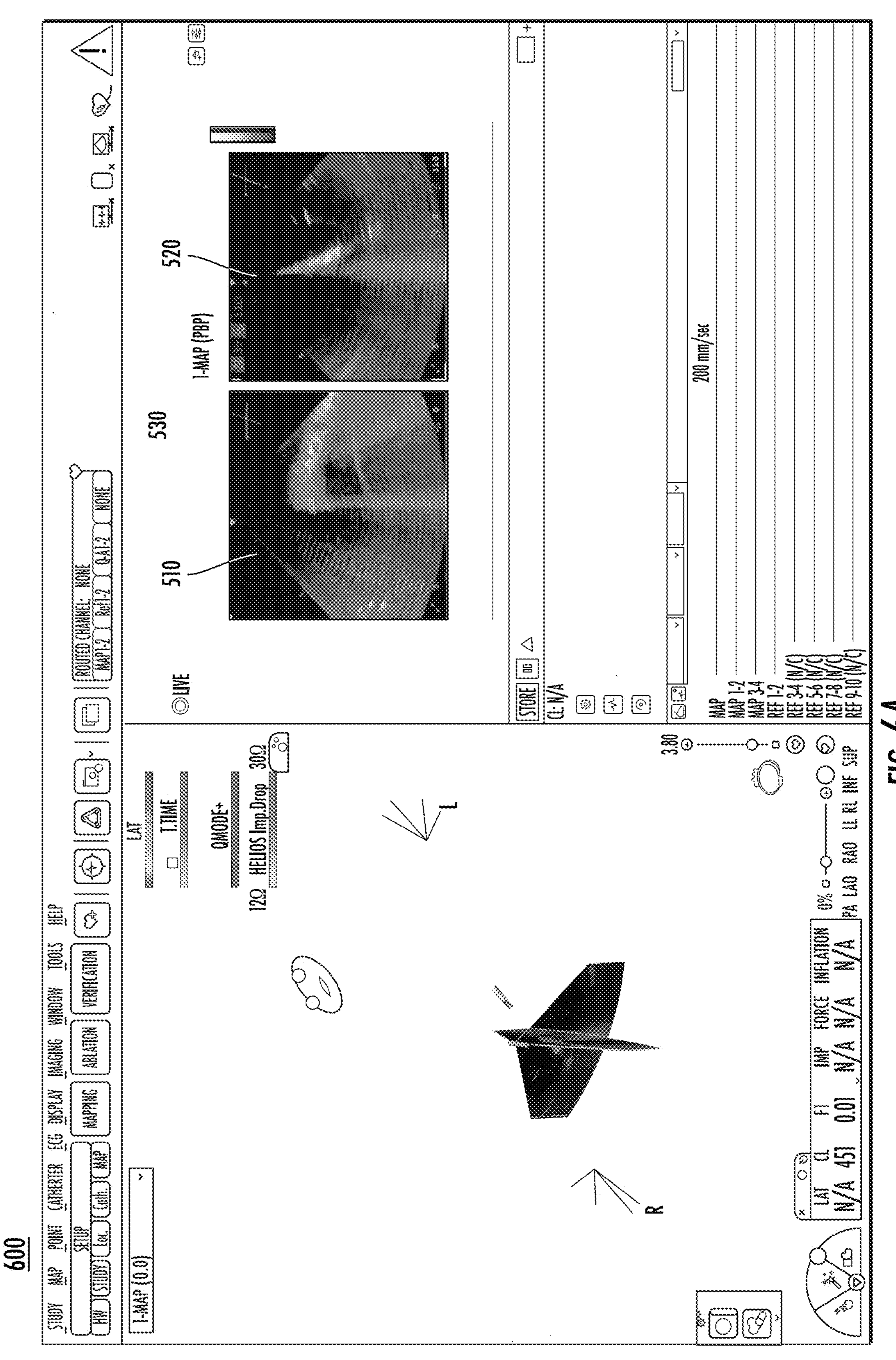
FIG. 6A illustrates a graphical user interface (GUI) that is configured to provide a user a tilt suggestion for tracking the ablation catheter tip.
Figure 6B:
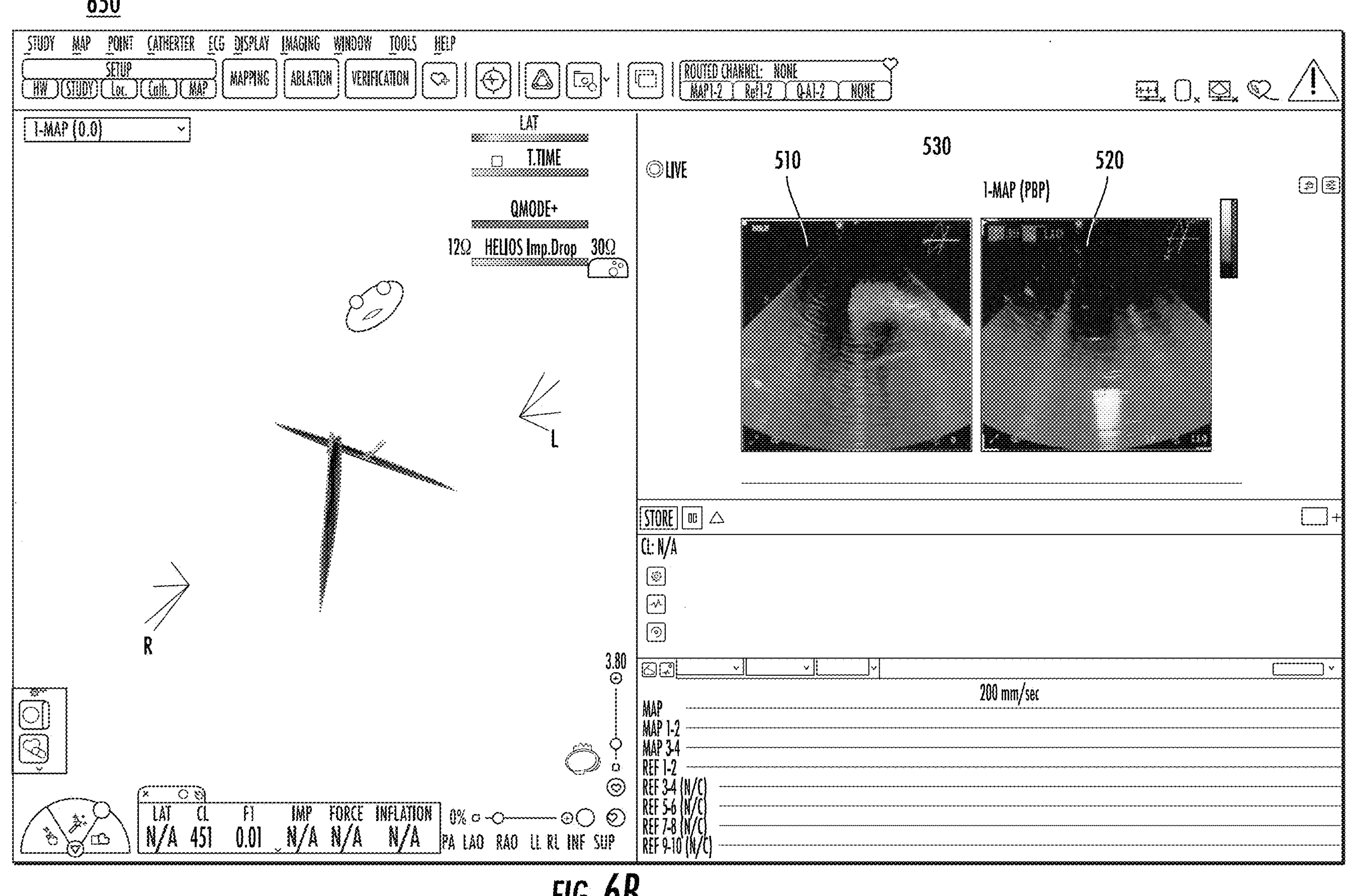
FIG. 6B illustrates a graphical user interface (GUI) that is configured to provide a user a tilt suggestion for tracking the ablation catheter tip.

FIG. 6A illustrates a graphical user interface (GUI) 600 that is configured to provide a user with a tilt suggestion for tracking the ablation catheter tip. Similarly, FIG. 6B illustrates a graphical user interface (GUI) 650 that is configured to provide a user with a tilt suggestion for tracking the ablation catheter tip. Collectively, GUI 600 and GUI 650 illustrate depictions of example tilt suggestions to track an ablation catheter tip. Each of GUI 600 and GUI 650 represent that changing the tilt to 39 degrees tracks the catheter tip (displayed in window 530). As described above with respect to FIG. 5, the first view window 510, second view window 520 and window 530 for the display of the tilt suggestion are included in each of GUI 600 and GUI 650.

Illustrated in both FIG. 6A and FIG. 6B is the graphical user interface of FIG. 5. Specifically, a first view window 510 and a second view window 520. Additionally, the tilt angle may be displayed in window 530 illustrated as part of second view window 520. As illustrated in the example windows of FIGS. 6A and 6B, a tilt angle of 39 degrees would enable a tracking of the catheter tip (illustrated in window 530). FIG. 6A represents the view before applying the suggested tilt angle and FIG. 6B represents the view after the suggested tilt angle is applied.

Referring specifically to FIG. 6A, there is illustrated a depiction in the biplane mode of the suggested angle of tilt. In the left portion of FIG. 6A left there is an illustration of the planes of the viewing fan (depicted in windows 510, 520) and the specific object, in this case a catheter. There are two planes of viewing provided represent the planes or an axis of view—in one case an axis depicted in window 510, and in the other an axis depicted in window 520. As is illustrated in the two windows 510, 520 of FIG. 6A, the viewing fan is not tracking the catheter. The offset angle needed to track the catheter is calculated as 39 degrees.

Referring specifically, to FIG. 6B, there is illustrated a depiction in the biplane mode of the suggested angle of tilt as compared to that of FIG. 6A, with FIG. 6B depicting the post tilt adjustment. In the left portion of FIG. 6B there is an illustration of the planes of the viewing fan (depicted in windows 510, 520) and the specific object, in this case a catheter. As with FIG. 6A, there are two planes provided which represent the planes or an axis of view—in one case an axis depicted in window 510, and in the other an axis depicted in window 520. As is illustrated in the two windows 510, 520 of FIG. 6B, the viewing fan is now tracking the catheter after the offset in FIG. 6A was accounted for.

Figure 7A:
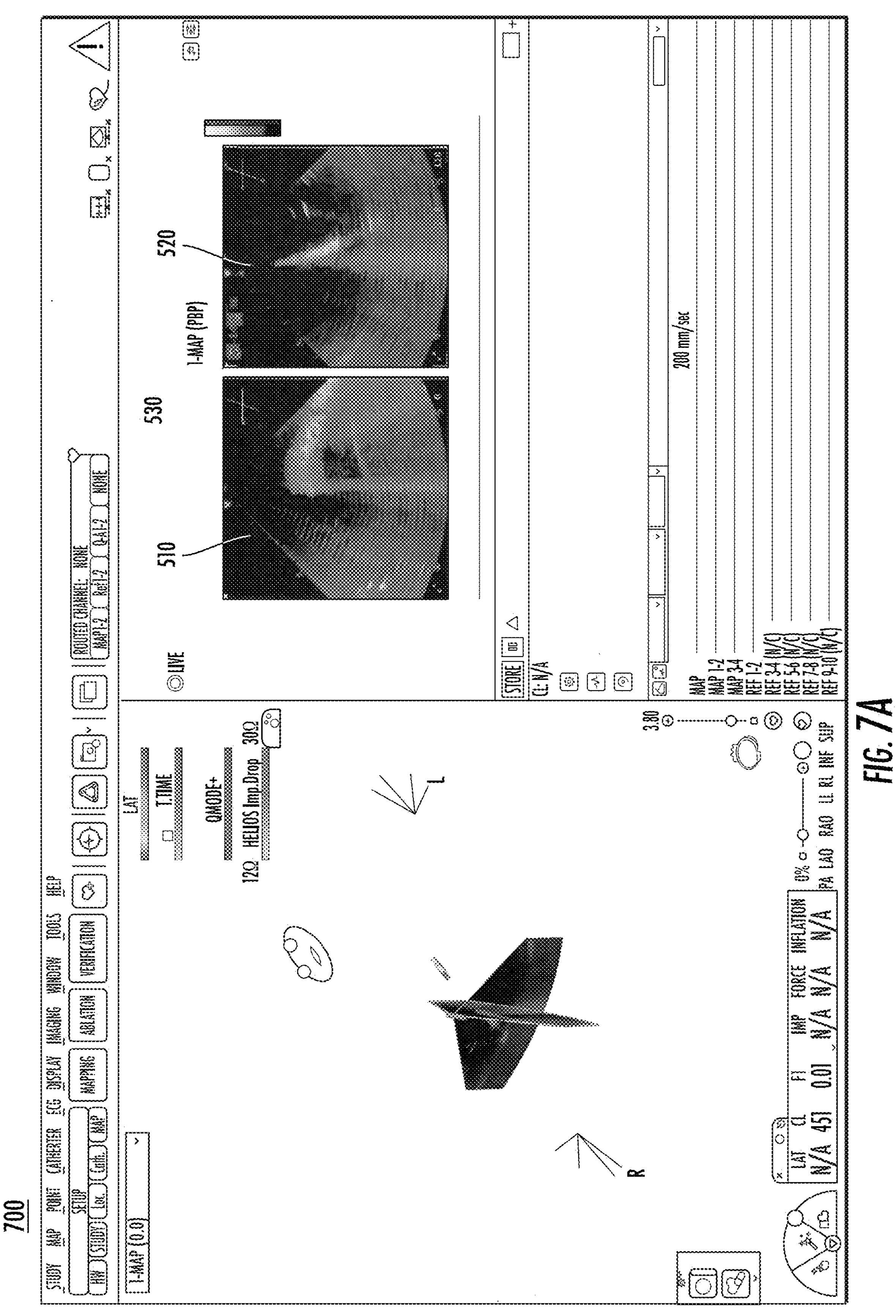
FIG. 7A illustrates a graphical user interface (GUI) that is configured to provide a user a tilt and rotation suggestion for tracking the ablation catheter tip and the direction of the ablation catheter tip.
Figure 7B:
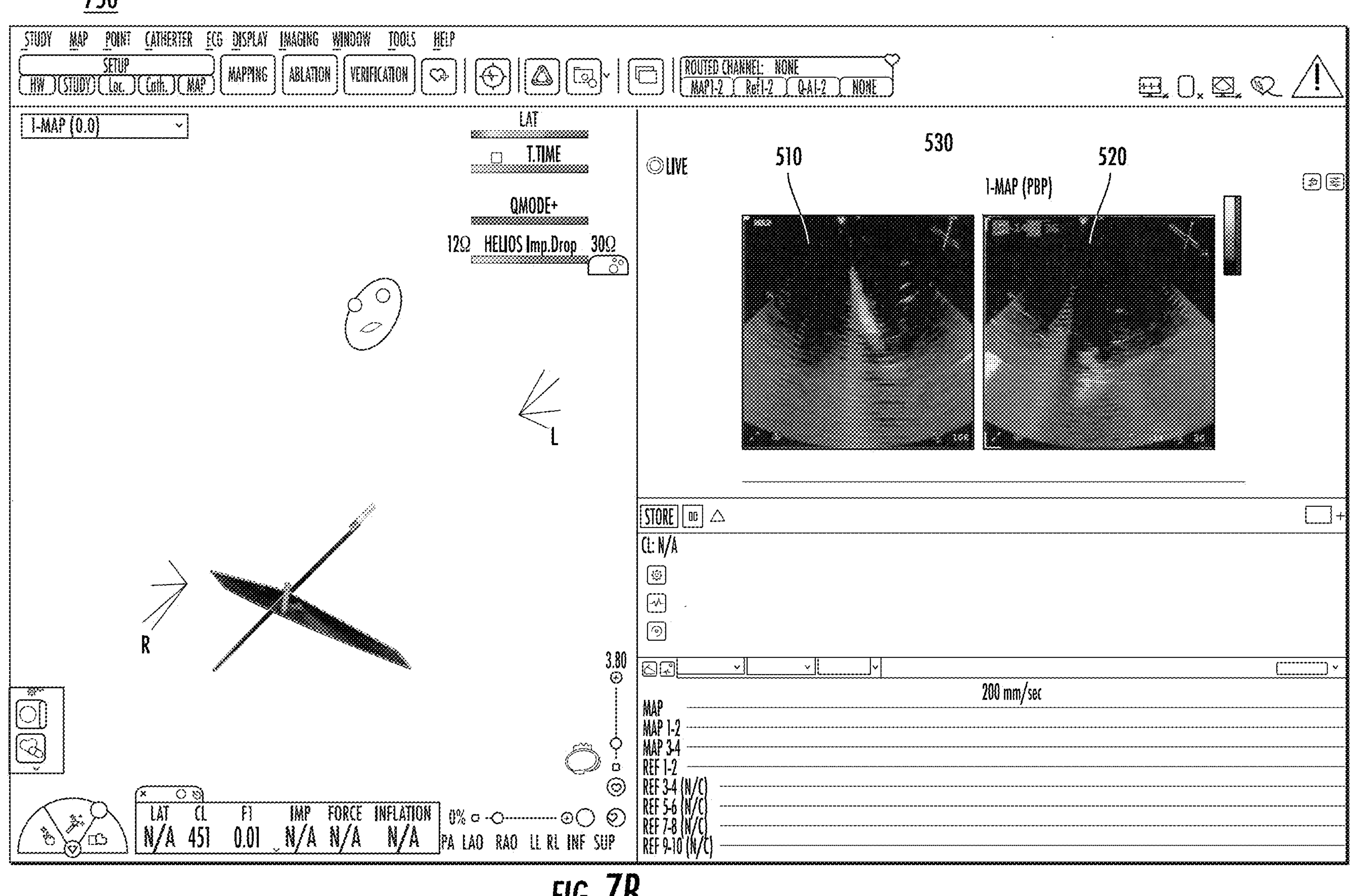
FIG. 7B illustrates a graphical user interface (GUI) that is configured to provide a user a tilt and rotation suggestion for tracking the ablation catheter tip and the direction of the ablation catheter tip.

FIG. 7A illustrates a graphical user interface (GUI) 700 that is configured to provide a user a tilt and rotation suggestion for tracking the ablation catheter tip and the direction of the ablation catheter. Similarly, FIG. 7B illustrates a graphical user interface (GUI) 750 that is configured to provide a user a tilt and rotation suggestion for tracking the ablation catheter tip and the direction of the ablation catheter. Collectively, GUI 700 and GUI 750 illustrate depictions of example tilt and rotation suggestions to track an ablation catheter tip and its direction. Each of GUI 700 and GUI 750 represent that changing the tilt to −14 degrees and rotation 34 degrees tracks the catheter tip (displayed in window 530). As described above with respect to FIG. 5, the first view window 510, second view window 520 and window 530 for the display of the tilt suggestion are included in each of GUI 600 and GUI 650.

Illustrated in both FIG. 7A and FIG. 7B is the graphical user interface of FIG. 5. Specifically, a first view window 510 and a second view window 520. Additionally, the tilt angle and rotation angle may be displayed in window 530 illustrated as part of second view window 520. As illustrated in the example windows of FIGS. 7A and 7B, a tilt angle of −14 degrees and a rotation angle of 34 degrees would enable a tracking of the catheter tip (illustrated in window 530). FIG. 7A represents the view before applying the suggested tilt and rotation angles and FIG. 7B represents the view after the suggested tilt and rotation angles are applied.

Referring specifically to FIG. 7A, there is illustrated a depiction in the biplane mode of the suggested angle of tilt and rotation. In the left portion of FIG. 7A left there is an illustration of the planes of the viewing fan (depicted in windows 510, 520) and the specific object, in this case a catheter. There are two planes of viewing provided represent the planes or an axis of view—in one case an axis depicted in window 510, and in the other an axis depicted in window 520. As is illustrated in the two windows 510, 520 of FIG. 7A, the viewing fan is not tracking the catheter. The offset angle in tilt and rotation needed to track the catheter is calculated as a tilt angle of −14 degrees and a rotation angle of 34 degrees.

Referring specifically, to FIG. 7B, there is illustrated a depiction in the biplane mode of the suggested angle of tilt and rotation as compared to that of FIG. 7A, with FIG. 7B depicting the post tilt and rotation adjustments. In the left portion of FIG. 7B there is an illustration of the planes of the viewing fan (depicted in windows 510, 520) and the specific object, in this case a catheter. As with FIG. 7A, there are two planes provided which represent the planes or an axis of view—in one case an axis depicted in window 510, and in the other an axis depicted in window 520. As is illustrated in the two windows 510, 520 of FIG. 7B, the viewing fan is now tracking the catheter after the offset angles in tilt and rotation in FIG. 6A was accounted for.

Figure 8:
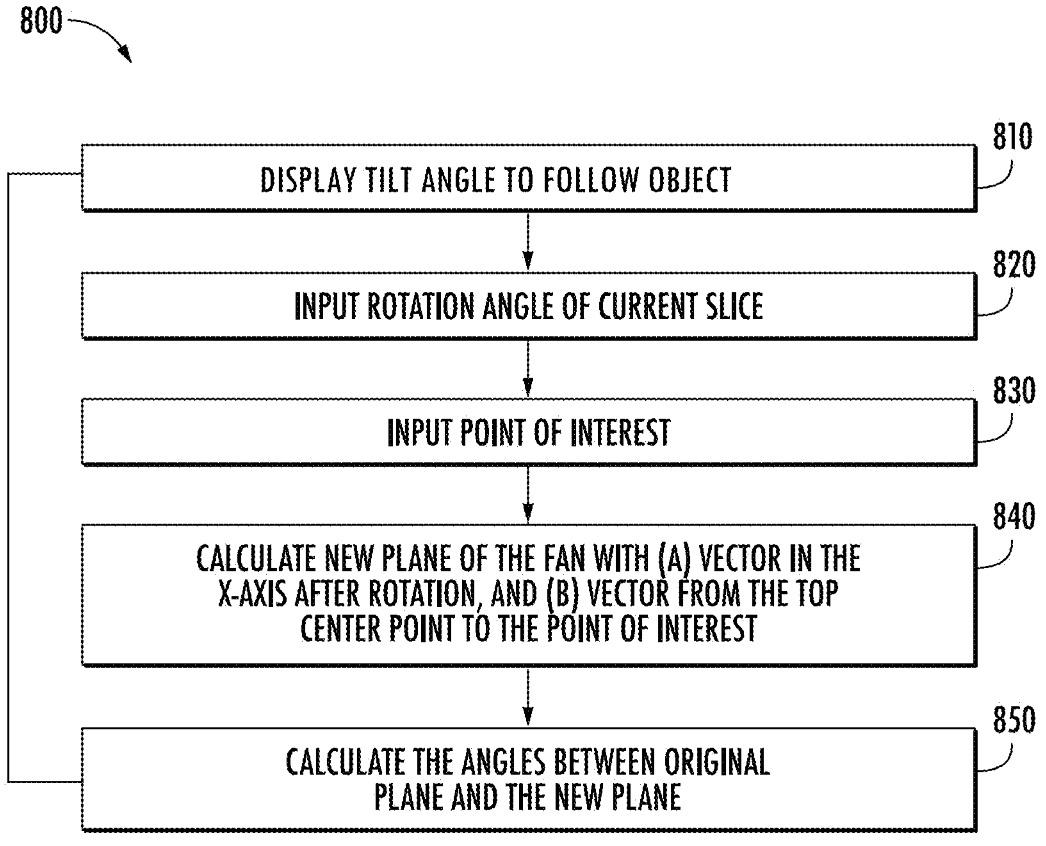
FIG. 8 illustrates a method of tracking a point of interest according to an example described herein.

FIG. 8 illustrates a method 800 of tracking a point of interest according to an example described herein. An example of a point of interest may include the ablation catheter tip, for example. Method 800 includes displaying a tilt angle to follow the point of interest (often referred to as an object, for example) to a user on a graphical user interface (GUI) at 810. At 820, method 800 includes inputting a rotation angle of a current slice of a view in the mapping into a processor associated with the GUI. The rotation angle is calculated by taking the orientation axis that is provided by the system, and calculating the angle between the axis currently and the axis needed to track the object. At 830, method 800 includes inputting a point of interest into a processor associated with the GUI which may include the transducer location, for example. These inputs may be system measured values, for example. For example in tracking a point of interest, the transducer location and the transducer rotation values may be used to create a matrix used to convert real-world coordinates to ULS coordinates. This matrix may be used to convert the object of interest coordinates in real-world coordinates to ULS coordinates.

At 840, in order to calculate the recommended tilt to track the ablation catheter tip, a calculation of the new plane of the fan is performed. The plane is represented by: (a) vector in the x-axis after rotation, the rotation is according to the rotate angle of the current slice, and (b) a vector from the tip center point to the point of interest. At 850, method 800 includes calculating the angles between the original plane and the new plane, such as based on Euler angles and suggests a new tilt angle, and providing a suggested tilt angle in absolute terms or as a delta angle from the current angle.

Figure 9:
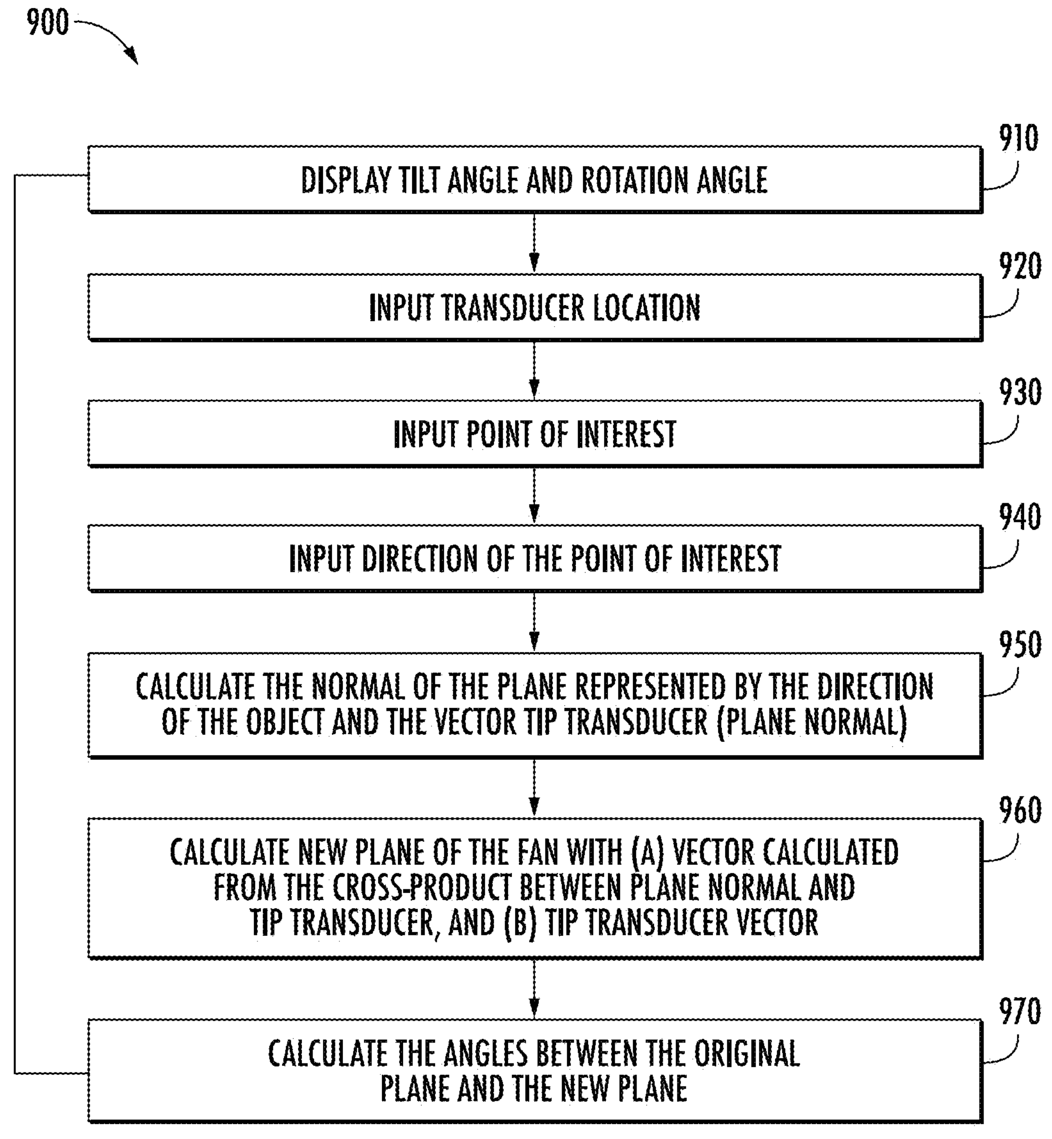
FIG. 9 illustrates a method of tracking a point of interest and a direction of the point of interest according to an example described herein.

FIG. 9 illustrates a method 900 of tracking a point of interest and a direction of the point of interest according to an example described herein. An example of a point of interest may include the ablation catheter tip, for example. Method 900 includes displaying a tilt angle and rotation angle to a user on a graphical user interface (GUI) at 910. At 920, method 900 includes inputting a transducer location into a processor associated with the GUI. At 930, method 900 includes inputting a point of interest into the processor associated with the GUI. At 940, method includes inputting a direction of the point of interest into the processor associated with the GUI. These inputs may be system measured values, for example.

At 950, method 900 includes calculating the normal of the plane represented by the direction of the point of interest (the object) and the vector tip of the transducer (plane normal). At 960, method 900 includes calculating a new plane of the fan (the location and direction of the ablation catheter tip appears on the ultrasound image) with (a) a vector calculated from the cross-product between the plane normal and the tip transducer, and (b) a tip transducer vector. This calculation may include the vector between the point of interest and the transducer location (scan origin) being calculated. This vector is referred to as tip2transducer. A calculation of the normal of the plane represented by the direction of the object and the vector tip2transducer is performed. This vector is referred to as plane Normal. A calculation is performed of the normal between the plane Normal and the tip transducer vector. This normal is referred to as Vector X. The new plane of the fan is calculated and represented by a vector that is calculated from the cross product between Vector X and tip transducer vector.

At 960, method 900 includes calculating the angles between the original plane and the new plane, based on Euler angles, and providing tilt and rotation angles in absolute terms or as a delta angles from the current angle.

In some examples, the points of interest of the tracked element and direction of the point of interest, such as the catheter's position on the CARTO® 3 System Location Pad coordinates, i.e., ablation catheter tip and its direction, may be based on the existing CARTO system magnetic localization technology. For example, in some configurations, the ultrasound catheter may not actually be moved by the system, and is instead controlled manually by the physician. Tracking in this context is directed to when the catheter is parked, the ultrasound beams, which are continuously emitted and received to form the volumetric wedge, described above, may be cropped, or have the beam gain/depths changed so that the relevant anatomy stays within view.

Although features and elements are described above in particular combinations, one of ordinary skill in the art will appreciate that each feature or element can be used alone or in any combination with the other features and elements. In addition, the methods described herein may be implemented in a computer program, software, or firmware incorporated in a computer-readable medium for execution by a computer or processor. Examples of computer-readable media include electronic signals (transmitted over wired or wireless connections) and computer-readable storage media. Examples of computer-readable storage media include, but are not limited to, a read only memory (ROM), a random-access memory (RAM), a register, cache memory, semiconductor memory devices, magnetic media such as internal hard disks and removable disks, magneto-optical media, and optical media such as CD-ROM disks, and digital versatile disks (DVDs). A processor in association with software may be used to implement a radio frequency transceiver for use in a WTRU, UE, terminal, base station, RNC, or any host computer.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Although features and elements are described above in particular combinations, one of ordinary skill in the art will appreciate that each feature or element can be used alone or in any combination with the other features and elements. In addition, the methods described herein may be implemented in a computer program, software, or firmware incorporated in a computer-readable medium for execution by a computer or processor. A computer readable medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire Examples of computer-readable media include electrical signals (transmitted over wired or wireless connections) and computer-readable storage media. Examples of computer-readable storage media include, but are not limited to, a register, cache memory, semiconductor memory devices, magnetic media such as internal hard disks and removable disks, magneto-optical media, optical media such as compact disks (CD) and digital versatile disks (DVDs), a random access memory (RAM), a read-only memory (ROM), an erasable programmable read-only memory (EPROM or Flash memory), a static random access memory (SRAM), and a memory stick. A processor in association with software may be used to implement a radio frequency transceiver for use in a terminal, base station, or any host computer.

The terminology used herein is for the purpose of describing particular embodiments only and is not intended to be limiting. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one more other features, integers, steps, operations, element components, and/or groups thereof.

The descriptions of the various embodiments herein have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A system for providing a suggested orientation of a 4D intracardiac echocardiogram (4D-ICE) catheter by tracking a target anatomy visually for display, the system comprising:

- a processor;
- an input/output (I/O) device configured to provide input to the processor and outputs from the processor;
- a graphical user interface (GUI) displayed on a display that is communicatively coupled to the processor, the GUI being used to monitor the catheter and configured to maintain inclusion of the target anatomy in an image field of view of the catheter during medical electrophysiology,
- the system configured to interface with the catheter, the catheter providing information to the processor via the I/O device, the system operating to:
- receive, as a first input, an angle of a current image plane of a view of the catheter;
- receive, as a second input, a point of interest related to the target anatomy;
- calculate a new image plane of view of the catheter using a vector in an axis after rotation and a vector from the catheter to the point of interest;
- calculate a tilt angle as a difference between the angle of the current image plane and an angle of the new image plane to provide for an angular motion of the catheter to maintain inclusion of the target anatomy in an image on the display;
- display on the GUI the calculated tilt angle configured for the catheter to track the target anatomy; and
- adjust the catheter by the tilt angle to the new image plane to thereby maintain the point of interest in the image on the display.

2. The system of claim 1 wherein the calculated tilt angle is multiplane.

3. The system of claim 2 wherein multiplane represents the tilt and rotation of the catheter.

4. The system of claim 1 wherein the catheter comprises views including at least one of dual-plane mode, multi-plane mode and 4D modes.

5. The system of claim 1 wherein the target anatomy is a vein.

6. A method for tracking a target to maintain inclusion of the target in a display of a device during a procedure, the method comprising:

displaying a tilt angle for causing the device to track the target of the procedure;

receiving, as a first input, an angle of a current plane of a view of the device;

receiving, as a second input, a point of interest related to the target;

calculating a new plane of the view of the device using a vector in an axis after rotation and a vector from the device to the point of interest;

calculating a tilt angle as a difference between the angle of the current plane and an angle of the new plane to provide for motion of the device to maintain inclusion of the target in the display; and adjusting the device by the tilt angle to the new plane of view thereby maintaining the point of interest in the display.

7. The method of claim 6 wherein the calculated tilt angles is multiplane.

8. The method of claim 7 wherein multiplane represents the tilt and rotation of the device.

9. The method of claim 6 wherein the new plane tracks the point of interest in the display.

10. The method of claim 6 wherein the device is a catheter and the target is a pulmonary vein.

11. A method for tracking a target and a direction of the target to maintain inclusion of the target in a display of a device during a procedure, the method comprising:

displaying, during the procedure, a tilt angle and a rotation angle for causing the device to track the target in the display;

receiving a device location, a point of interest related to the target, and a direction of the point of interest;

calculating a normal of a plane represented by the direction of the point of interest and the device location;

calculating new plane of a view of the device using a vector calculated from a cross-product between the calculated normal of the plane and a vector of the device, and the vector of the device; and calculating the angles between a current plane of the device represented by the calculated normal of the plane and the calculated new plane of view of the device.

12. The method of claim 11 wherein the angles are multiplane.

13. The method of claim 12 wherein the multiplane represents a tilt and rotation of the device.

14. The method of claim 11 further comprising changing the angles of the device to the new plane of view of the device.

15. The method of claim 14 wherein the new plane tracks the target.

16. The method of claim 11 wherein the device is a medical probe.

17. The method of claim 16 wherein the target is a part of a patient body.

18. The method of claim 11 wherein the device is a catheter and the target is a pulmonary vein.

19. The method of claim 11 wherein the device is four-dimensional catheter with views comprising dual plane mode, multi-plane mode and 4D.

20. The method of claim 11 wherein the device comprises a transducer of a catheter.

* * * * *